(12) United States Patent
Kabir

(10) Patent No.: US 11,972,865 B1
(45) Date of Patent: Apr. 30, 2024

(54) HIGH PROBABILITY DIFFERENTIAL DIAGNOSES GENERATOR AND SMART ELECTRONIC MEDICAL RECORD

(71) Applicant: Azad Alamgir Kabir, Biloxi, MS (US)

(72) Inventor: Azad Alamgir Kabir, Biloxi, MS (US)

(*) Notice: Subject to any disclaimer, the term of this patent is extended or adjusted under 35 U.S.C. 154(b) by 676 days.

(21) Appl. No.: 15/356,933

(22) Filed: Nov. 21, 2016

Related U.S. Application Data

(63) Continuation-in-part of application No. 13/948,246, filed on Jul. 23, 2013, now Pat. No. 9,536,051.

(60) Provisional application No. 62/273,189, filed on Dec. 30, 2015, provisional application No. 61/675,779, filed on Jul. 25, 2012.

(51) Int. Cl.
| | |
|---|---|
| *G16H 50/20* | (2018.01) |
| *G06F 3/0482* | (2013.01) |
| *G16H 70/20* | (2018.01) |
| *G06F 3/0354* | (2013.01) |
| *G06F 3/04883* | (2022.01) |
| *G06F 3/0489* | (2022.01) |

(52) U.S. Cl.
CPC ........... *G16H 50/20* (2018.01); *G06F 3/0482* (2013.01); *G16H 70/20* (2018.01); *G06F 3/03545* (2013.01); *G06F 3/04883* (2013.01); *G06F 3/0489* (2013.01)

(58) Field of Classification Search
CPC ......... G16H 50/70; G16H 50/20; G16H 70/20
See application file for complete search history.

(56) References Cited

U.S. PATENT DOCUMENTS

| | | | | |
|---|---|---|---|---|
| 5,517,405 A | * | 5/1996 | McAndrew | G16H 10/20 706/45 |
| 5,724,968 A | * | 3/1998 | Iliff | G06F 19/3418 600/300 |
| 6,468,210 B2 | * | 10/2002 | Iliff | G06Q 50/22 600/300 |
| 6,643,644 B1 | * | 11/2003 | Furusho | G06F 16/9017 |
| 2002/0029157 A1 | * | 3/2002 | Marchosky | G06F 19/3418 705/3 |
| 2003/0154110 A1 | * | 8/2003 | Walter | G06F 19/3418 705/3 |
| 2004/0153338 A1 | * | 8/2004 | Kim | G06F 19/328 705/2 |
| 2005/0027670 A1 | * | 2/2005 | Petropoulos | G06F 16/9535 |
| 2009/0007924 A1 | * | 1/2009 | Iliff | G06F 19/3418 128/898 |
| 2011/0105979 A1 | * | 5/2011 | Schlaeper | G16H 10/20 604/5.01 |
| 2012/0182291 A1 | * | 7/2012 | Rawat | G06T 17/00 345/419 |

\* cited by examiner

*Primary Examiner* — Marc S Somers
(74) *Attorney, Agent, or Firm* — The Iwashko Law Firm, PLLC; Lev Ivan Gabriel Iwashko

(57) ABSTRACT

A method for performing an automated medical diagnosis of a patient and for providing and utilizing a smart electronic medical record to assist in confirming diagnosis of a patent. The diagnosis will be based upon a patient's signs/symptoms/findings which are input by a user/heath care provider and then further analyzed to then output a listing of high probability differential diagnoses/diseases and a low probability differential diagnoses/diseases that the patient may have. This analysis assists health care providers in providing a fast and early indication of potential conditions based upon an analysis of a patient's signs/symptoms/findings.

13 Claims, 28 Drawing Sheets

Assessment and Plan ⸺ 93
Pneumonia
Patient needs to be seen by provider
⸺ 94
Calculate CURB score by adding the score from below:
⸺ 95
Confusion (present = 1; absent = 0)
BUN > 19 mg/dl (>7 mmol/L) (present =1; absent =0)
Respiratory rate > 30/min (present = 1; absent = 0)
Systolic BP < 90 mmHg or Diastolic BP 60 mmHg(present = 1; absent=0)

CALCULATED CURB SCORE 3 OR MORE: PATIENT NEEDS TO BE HOSPITALIZED
CALCULATED CURB SCORE 2 OR LESS. PATIENT CAN BE SENT HOME
Laboratory and Radiological Studies
⸺ 96

Complete blood count

Blood culture ⸺ 96A
Sputum for Gm stain, Culture and sensitivity (C&S)
Chest X-Ray
ABG [if patient is hypoxic]

Treatment ⸺ 97

Please select one of the treatment group:
Treatment regimens for outpatients with community-acquired pneumonia(CAP):
⸺ 97B
No Comorbidites
Azithromycin 500 mg PO on day one followed by four days of 250 mg a day Or
Azithromycin 500mg po daily for 3 days
Clarithrmycin 500mg po twice a day
Doxycycline 100 mg PO twice daily for seven days With comorbidities:
Levofloxacin 750 mg PO daily for five days
Moxifloxacin 400 mg PO daily for five days
Gemifloxacin 320 mg PO daily for five days
Combination therapy with one of the following
Amoxicillin 1g PO three times daily Or
Amoxicillin-clavulanate 2 g PO twice daily Or ⸺ 97A
Cefpodoxime 200 mg PO twice daily Or
Cefuroxime 500 mg PO twice daily
PLUS one of the following

Fig. 9B

Date/time: 01/01/2016; 7:30 AM

① MRI Brain c̄ out contrast (stroke) ASAP.

② AM Lab: CBC, CMP.

90B

Free text type your order using key board

Date and Time: 01/01/2016; 7:30 AM

1. MRI BRAIN without contrast (stroke)
2. AM lab CBC, CMP
3. Get orthostatic vital sign now.
4. Call MD if patient blood pressure < 90 or temperature > 100.

SUBMIT ORDER / PHYSICIAN MUST SIGN BEFORE SUBMIT

90C

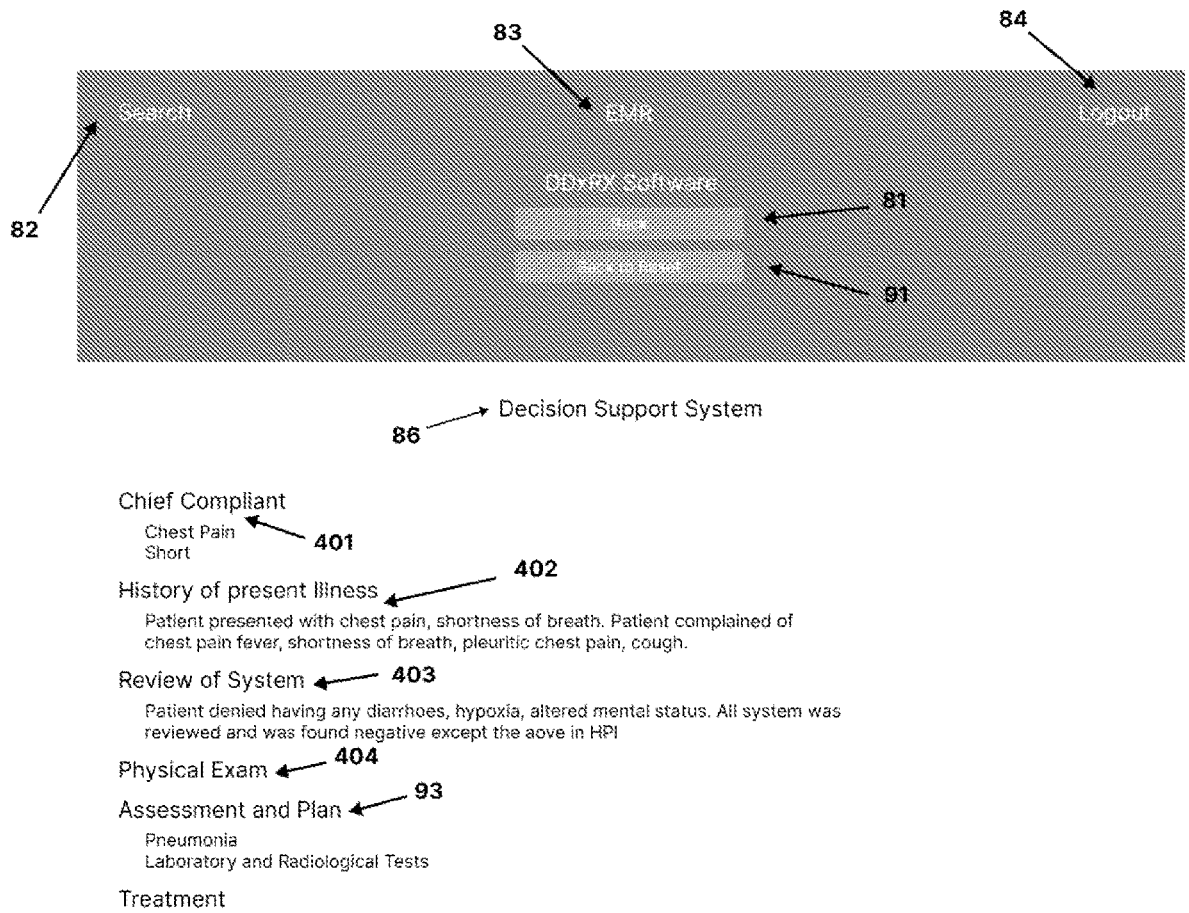

→ Decision Support System
86

Chief Compliant
  Chest Pain ← 401
  Short
History of present Illness ← 402
  Patient presented with chest pain, shortness of breath. Patient complained of chest pain fever, shortness of breath, pleuritic chest pain, cough.
Review of System ← 403
  Patient denied having any diarrhoes, hypoxia, altered mental status. All system was reviewed and was found negative except the aove in HPI
Physical Exam ← 404
Assessment and Plan ← 93
  Pneumonia
  Laboratory and Radiological Tests
Treatment

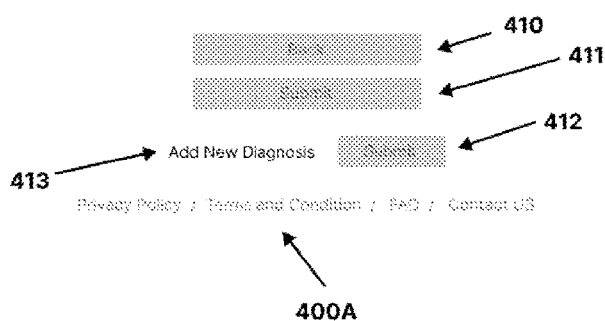

HIGH PROBABILITY DIFFERENTIAL DIAGNOSES GENERATOR AND SMART ELECTRONIC MEDICAL RECORD

CROSS REFERENCE TO RELATED APPLICATIONS

This application is a (1) Continuation-In-Part application relying on applicants' previously filed application Ser. No. 13/948,246 filed on Jul. 23, 2013 which claims the benefit of U.S. provisional application Ser. No. 61/675,779 filed on Jul. 25, 2012, and also claims the benefit of U.S. provisional application Ser. No. 62/273,189 filed on Dec. 30, 2015.

TECHNICAL FIELD

The present invention relates, in general to automated diagnoses tools and, more particularly, to a high probability differential diagnoses generator to be used during patient care by a health care provider.

BACKGROUND OF INVENTION

The diagnostic thinking is defined as the process of hypothesis generation and testing. Therefore, the hypotheses generated at the beginning of a physician-patient encounter usually frames and structures the diagnosis, modulating its efficiency and accuracy. The initial hypotheses, although it may be modified by subsequent data, guides the physician's inquiry. The patient interview naturally elicits one or more hypotheses from the beginning. Sometimes a hypothesis is formulated even before the patient interview. This "working hypothesis" constrains not only the rest of the interview, but any subsequent hypotheses generation—which of course must also be tested.

Sometimes, physicians generate a diagnostic hypothesis early in the encounter. In fact, some physicians develop a working hypotheses during the first 50 seconds of a patient consultation. Some studies indicate that physicians form diagnostic hypotheses extremely early in the clinical encounter, and that the mean number of hypotheses under consideration at any time is between two and four.

Since the early generation of hypotheses is, and should be, the rule rather than the exception, it follows that one of the early hypotheses should have a reasonably high probability of being correct, to justify the elaborate system of history taking, physical examination, and the like.

In fact, focusing on an incorrect hypothesis and not considering alternative diagnoses is one of the major causes of diagnostic error. Under basic rules of diagnostic reasoning, within a minutes of a patient encounter (preferably with in 1-2 minutes), a health care provider, namely a physician and/or nurse, should generate at least 2-4 epidemiology-based hypotheses (i.e. rank-ordered hypotheses based on age-sex distribution of disease condition). Differential diagnosis should be heterogeneous or diverse. Diagnostic efficiency and accuracy depends on the quality of the hypotheses generated (i.e. how well the presumed differential diagnoses fits patient signs, symptoms and clinical findings). Experienced physicians usually formulate hypotheses and diagnostic plans very quickly, and the quality of their hypotheses is much better compared to that of novice physicians. Novice physicians often do not know how to generate appropriate hypotheses, they struggle to develop a diagnostic plan, and they have difficulty in establishing diagnostic possibilities from the collection of patient data.

The rank ordering of the generated hypotheses is also very important for effective diagnostic decision making. This rank ordering primarily depends on the epidemiological distribution of disease (determined by patient's age, sex, and clinical characteristics). Expert physicians will likely have an advantage over novices in term of rank ordering differential diagnoses as they learn over the years the distribution of diseases via clinical practice.

Currently, there are books that list all possible disease conditions a patient can have if a single sign or symptom or clinical finding is present. But every disease is related to multiple signs or symptoms or clinical findings and a single sign, symptom or clinical finding is linked to a number of disease or differential diagnoses. Also, these lists of diseases in books or elsewhere will also include diseases that are very rare or uncommon. If someone wants to consider all the available differential diagnoses linked to a given sign, symptom or finding during every patient encounter, the time and costs associated with such a visit would increase leading to increased health care costs, and increasing the risk of diagnostic error and creating an ineffective health care system.

There are many electronic medical records that currently exist in the market for the healthcare providers. However, a majority of these records are disliked by the physician as they are not efficient, and they create inconvenience in the physician work flow. In paper chart medical records, a physician is able to write an order as if he or she is writing in a paper chart. Paper chart was and still is the most efficient style of patient care delivery. This invention will deliver the paper chart experience to physician.

Moreover, existing electronic medical records are not linked to and part of systems containing algorithms to help a healthcare provider to find a correct diagnosis based on a present clinical problem and there is no such medical record that can automatically suggest evidence based laboratory and radio-logical tests and treatment strategies associated with a diagnosis—modern electronic records fail to aid in diagnostic decision making. Further, currently existing electronic medical records require that a physician go through many steps to accomplish one task—such as ordering medication. For example, a physician has to search the drug in order search box, select a name from drop down box and then select dose specification, and put comments and ultimately submit the order. There is a need for a system that will allow a physician to achieve such tasks under a faster process.

Thus, there is a need for an electronic medical record that will deliver these additional services and also provide the paper chart experience to a physician. In addition, there is no software available to health care providers that can process multiple signs, symptoms and clinical findings to generate a short list of high probability differential diagnoses that are clinically meaningful. Accordingly, a need exists in the art for a system and method that allows health care providers to analyze patient data and generate a high probability differential diagnoses during patient care.

BRIEF SUMMARY OF THE INVENTION

The present invention is directed to a system and method for providing an electronic medical record and analyzing and comparing data, such as patient data, signs, symptoms, and clinical data, and utilizing that data to generate a differential diagnoses for a particular patient to assist a health care provider in quickly generating a number of potential early hypotheses relating to a patient's condition with a reasonably high probability of being correct and providing the health care provider with various data relating to the potential condition, such as tests needed, treatment options, and severity of condition.

In one embodiment, the present invention will analyze patient conditions, signs, and symptoms and generate a differential diagnoses to assist health care providers in treating patients. The embodiment may also rank order the differential diagnoses based on various criteria considered during the diagnosis.

In one embodiment, the present invention will allow a healthcare provider to input patient data, such as signs, symptoms, and other data such as clinical findings and utilize that data to generate a high probability differential diagnosis to reduce potential errors in diagnosis usually seen in expert vs novice diagnosis of patients. In such an embodiment, an average of 2 to 6 high probability diagnoses can be presented to a health care provider for consideration in treating patients. The present invention will also utilize various data for the purpose of providing test ordering strategy and disease management strategies.

In another embodiment, the present invention can also generate a low probability differential diagnosis for the purpose of assisting health care providers in diagnosing and locating rate diseases among patients.

The present invention may also include the ability to edit, create, and access electronic medical records of patients that may be used during the diagnosis process. The present invention may also analyze and gather data from the electronic medical record and use data from the medical record during the diagnosis process. The invention may also be configured to enable a user to enter free-form handwritten text and notes into the medical record as a means to document a user's notes about the patient without the need for a paper medical record.

The present invention can help any healthcare provider to process a patient's signs/symptoms/findings (SSF) in a manner that one will be able to quickly focus on the most likely diagnoses. The present invention will also enable any mid-level health care provider, nurse practitioner or physician assistant to evaluate and process medical data in an effective fashion. Most importantly, the present invention can be an asset for the academic and training environment where medical residents and students deliver patient care, as it may help them avoid diagnostic error and avert unnecessary health care expenditure by reducing diagnostic work-up. Moreover, nurses can educate themselves about a patient's presenting diagnoses and provide important data to the physician and they can even provide diagnostic work up reminders to respective health care providers. Overall the present invention can work as a reminder system for critical diagnoses and improve patient safety.

In addition, one embodiment of the present invention is a smart electronic medical record that can help prevent diagnostic error, prevent unnecessary testing, help increase quality of care and reduce length of stay and readmission. In one embodiment, a nurse or any health care provider starts patient triage by completing an artificial intelligent decision support system popped up by electronic medical record. The diagnostic confirmation algorithm utilizes yes and no questions based on diagnostic criteria of certain diagnosis. This algorithm can help a nurse decide routine style (non-urgent) physician notification verses urgent (STAT) notifications. In addition, the present invention may enable to nurse to run an intelligent decision support system when new abnormal labs are available. A case manager/user may even run intelligent decision support system while patient is discharged in order to help prevent readmission of the patient.

The present invention may also include a blank order entry page to allow physicians to enter orders similar to a paper chart. It includes hand writing using a pen in touch screen computer and free text typing using key board in a blank page. Nurses are also able to utilize the present invention to assist a physician in collect presenting clinical signs and symptoms that ultimately help develop a physician encounter note.

The foregoing has outlined rather broadly the features and technical advantages of the present invention in order that the detailed description of the invention that follows may be better understood. Additional features and advantages of the invention will be described hereinafter, which form the subject of the invention. It should be appreciated that the conception and specific embodiment disclosed may be readily utilized as a basis for modifying or designing other structures for carrying out the same purposes of the present invention. It should also be realized that such equivalent constructions do not depart from the invention. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which:

FIGS. 9A-9G illustrate screen shots of an embodiment of the present invention;

FIG. 11 illustrates a screen shot of an embodiment of the present invention;

DETAILED DESCRIPTION OF THE INVENTION

Figure 1:
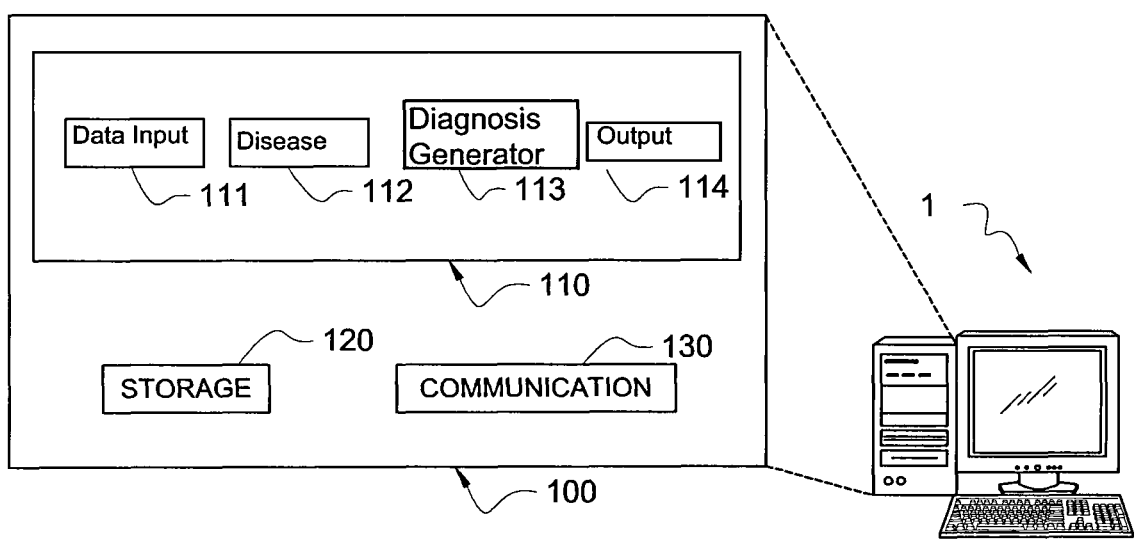
FIG. 1 is an illustration of a general architecture of a system of one embodiment of the present invention.

FIG. 1 is a diagram illustrating patient data input-disease-differential diagnoses-output environment 100 according to one embodiment of the present invention implemented on computer 1 for analyzing patient signs/symptom data to perform a differential diagnosis and generate diagnoses for a user/health care provider treating a particular patient. A health care provider, such as a physician and/or a nurse, can collect patient data and input that data to the present invention. That inputted data along with other data, such as clinical data, various disease data, and the like will be compared and analyzed by present invention so that a differential diagnosis can be output by the present invention to assist the health care provider in providing care to a patient based upon the output from the present invention. In addition to data input-disease-differential diagnoses-output environment 100, the computer system may include an operating system, a computer's coordinating program that is built on the instruction set for a processor or microprocessor, and the hardware that performs the logic operations and manages the data movement of the computer.

Data input-disease-differential-diagnoses-output environment 100 represents one application running on computer 1. In one embodiment of the present invention, data input-disease-differential diagnoses-output environment 100 includes diagnosis module 110, storage module 120, and communication module 130. Diagnosis module 110 may also include data input sub-module 111, disease sub-module 112, diagnosis generation sub-module 113 and output sub-module 114. Data input-disease-differential-diagnoses-output environment 100 is advantageous as it may be used to analyze various health care related data, such as patient signs, symptoms, and clinical data associated with a patient and then compare and analyze that data against other data, such as a disease database to generate a differential diagnosis that may be ranked in a number order based on a priority of high to low probability. This generated differential diagnosis may then be used by the health care provider to treat a patient accordingly.

Although FIG. 1 illustrates diagnosis module 110 with only four sub-modules, data input sub-module 111, disease sub-module 112, diagnosis generation sub-module 113 and output sub-module 114, the present invention is not limited to this configuration. In alternative embodiments of the present invention, diagnosis module 110 may include several other sub-modules in addition to sub-modules 111, 112, 113, and 114.

Storage module 120 enables the saving and storing of data, such as patient data, disease data, differential diagnosis data, and other related medical data. After a differential diagnosis has been generated, storage module 120 allows a user, such as a health care provider, to save the differential diagnosis and any related reports or data. Storage module 120 may also allow a user to save any specific data that is analyzed during the data analysis, and differential diagnosis generation process. For example, if the data analysis reveals a pattern of a particular differential diagnosis for a particular geographic region, patient age group, or patient gender type, a user can store various details and/or notes that can be retrieved at a later date by a user.

Communication module 130 enables a user to communicate with others and access external databases located in remote locations when in the process of analyzing data in using the present invention. In one embodiment of the present invention, this is accomplished by communication module 130 handling any data, such as retrieving various medical data that may be stored on and retrieved from an external third party database, such as databases storing clinical data, medical journals or articles or even patient data that may be stored in an external database. Communication module 130 may communicate data, such as medical data, differential diagnoses for patients, patient data or data reports to third parties, such as health care providers at different locations, by, sending an electronic message, sending an email, sending an Short Message Service (SMS) message, sending a text message, any combination of the above, and the like.

Diagnosis module 110 will query and analyze data, such as patient data that may be input by a health care provider when interviewing or meeting with a patient. In addition, diagnosis module 110 may also process all the signs, symptoms or clinical findings associate with or related to a patient and generate a short list of high probability differential diagnoses. Generation of such a list will help reduce diagnostic error and improve patient safety. Diagnosis module 110 may also act as a reminder system for health care providers and can also act to avert diagnostic error by generating the short list of high probability diagnoses. All human diseases are linked to a set of clinical signs, symptoms and clinical findings. A sign, symptom or clinical finding (SSF) may be present in multiple diseases. For example, a fever (a symptom) can be present in pneumonia, a urinary tract infection, sepsis, cellulitis, a pulmonary embolism, and many other conditions. Diagnosis module 110 may analyze the signs, symptoms, or clinical findings (SSF) related to a patient and then compare this patient data to a database of signs, symptoms or clinical findings that are linked to multiple diseases (called differential diagnoses) to ultimately provide a differential diagnosis for the health care provider. The present invention may be configured so that in includes an internal database of signs, symptoms or clinical findings or the present invention may be configured to connect to or communicate with external databases containing such information in addition to other related medical information to assist in generating a differential diagnosis.

Inputting data, such as patient data, may be accomplished via data input sub-module 111. Data sub-module 111 may function to intake and store all data input by a health care provider, such as patient data. Such patient data may include various types of data regarding a patient, such as name, date of birth, weight, height, race, gender, current medical conditions, current medications, surgery history, family medical history, current signs and symptoms, blood pressure, and the like. Any data input by a user/health care provider will be managed and handled by data sub-module 111. In one embodiment, data sub-module 111 may create a data record for all data input for a particular patient and may then store that data in a database or other storage system. Data sub-module may also be configured to provide a means for obtaining data through various means, such as user input with a keyboard or other device, use of barcodes, quick response (QR) codes, electronically scan-able or readable labels and the like.

In an embodiment of the present invention, disease sub-module 112 may operate to interface data input sub-module 111 and diagnosis generator sub-module 113 with an internal database of diseases or medical conditions and/or the signs, symptoms or clinical findings related to said diseases or medical conditions. Disease sub-module 112 may also be configured to connect to or communicate with external databases containing various medical information that can be accessed for use in generating a differential diagnosis based upon various patient data input through data input sub-module 111. In addition, the querying of data, such as medical data, from different data sources may be accomplished by disease sub-module 112. In one embodiment of the present invention, disease sub-module 112 may query data from any data source, such as databases of available medical journals, studies, diseases, statistical data, and various historical medical data that are maintained by various third party providers. The present invention is not limited to querying data from internal databases or the third party databases discussed herein as the present invention may query data from any available source now existing or which may be created in the future. In querying data from different data sources, disease sub-module 112 may search for any number of types of relevant data, such as the disease data prevalent among particular age groups, gender, or particular geographic regions, and the like.

In an embodiment of the present invention, diagnosis generation sub-module 113 will analyze patient data input via data input sub-module 111 and interface and gather disease or medical condition data from disease sub-module 112 so that a differential diagnosis may be generated. Diagnosis generation sub-module 113 may analyze patient data, such as the medical signs, symptoms and clinical findings that a patient is experiencing, and then extract and gather all potential diseases or medical conditions from disease sub-module 112 that are common among the presenting signs, symptoms, or clinical findings of the patient. In gathering the diseases associated with the patient's signs and symptoms, diagnosis generation sub-module 113 can order the diseases based upon the common signs or symptoms present in the diseases and can then generate a short list of high probability differential diagnoses or the least number of diagnoses that explain a majority of the present signs, symptoms or clinical findings. Thus, diagnosis generation sub-module 113 can provide a short list of the most likely set of diseases or medical conditions that a patient may have and then find a diagnosis or the least number of diagnoses that may explain all of or most of the present signs, also known as Ockham's razor. This short list will be called high probability differential diagnoses as they explain all the presenting signs, symptoms, or clinical findings. In generating this short list of the most likely set of diseases or conditions that a patient can have, the present invention may save health care expenditure by reducing unnecessary diagnostic work up.

Formatting and putting together reports that may be used by health care providers or users for use during patient diagnosis and treatment may be accomplished via output sub-module 114. Output sub-module 114 will handle data, such as data generated by diagnosis generator sub-module 113, and can then take that generated data and assemble, create, and output any number of reports, specific data fields, and the like that a health care provider/user may use when providing care or treatment to a patient. For example, output sub-module 114 can generate a report for a particular patient that contains individual data about a patient's medical condition and can also include on the report a listing of potential diseases and/or conditions that the patient may have based upon the diagnosis generated by diagnosis generator 113. In some embodiments, output sub-module 114 may also create disease history reports that keep track of the various disease and/or conditions that were generates as a potential patient disease or condition so that health care providers can access the data for later use including, but not limited to, keep track of various trends related to diseases or conditions. For instance, the present invention may generate and store reports in a database that allow health care providers to track the most prevalent disease or condition existing among patients of a certain age, race, and gender for a particular geographic region during a particular time or year.

The program code segments making up data input-disease-differential-diagnoses-output environment 100 can be stored in a computer readable medium or transmitted by a computer data signal embodied in a carrier wave, or a signal modulated by a carrier, over a transmission medium. The "computer readable medium" may include any medium that can store or transfer information. Examples of the computer readable medium include an electronic circuit, a semiconductor memory device, a ROM, a flash memory, and erasable ROM (EROM), a floppy diskette, a compact disk CD-ROM, an optical disk, a hard disk, a fiber optic medium, a radio frequency (RF) link, etcetera. The computer data signal that can propagate over a transmission medium such as electronic network channels, optical fibers, air, electromagnetic, RF links, etcetera. The code segments may be downloaded via computer networks such as the Internet, Intranet, and the like.

Figure 2:
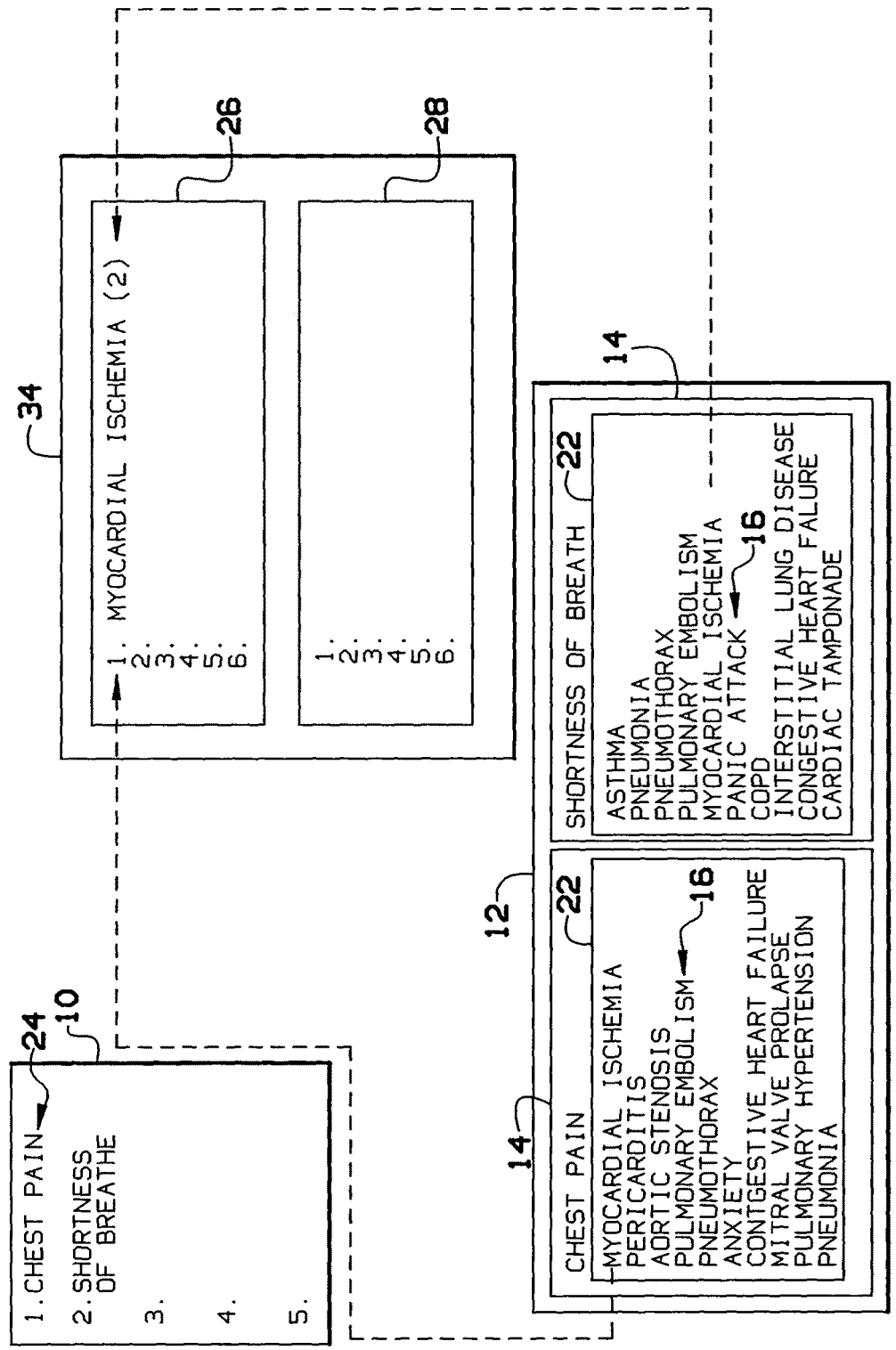
FIG. 2 illustrates a schematic exemplary view of an embodiment of the present invention.

FIG. 2 illustrates a schematic exemplary view of an embodiment of the present invention. Illustrated in FIG. 2 is input list 10 with a plurality of inputs 24. While FIG. 2 only illustrates five inputs 24, the present invention is not limited to five inputs as the present invention may have any number of inputs 24. Inputs 24 are preferably the signs/symptoms/findings that a patient is experiencing which may be inputted or selected by a user, such as a health care provider, when the heath care provider is interviewing or obtaining information from an individual/patient. Inputs 24 may consist of conditions a patient is experiencing and may also include laboratory data, radiological data, vital signs, clinical findings and the like. In one embodiment, input list 10 is created by the user/health care provider selecting or inputting inputs 24 during a patient interview or treatment. For instance, when a health care provider is interviewing a patient who is experiencing chest pain and shortness of breath, then the health care provider can input or select these symptoms 24 as illustrated in FIG. 2. In inputting or selecting symptoms/inputs 24, a health care provider will preferably input or select the symptoms 24 based upon the severity or importance of the symptoms. Thus, a health care provider in interviewing a patient will preferably input the symptoms 24 based upon his/her analysis of the patient's condition making sure to input the symptoms 24 so that the most severe or important symptom is input first followed by the next important or severe symptom 24. Thus, in FIG. 2, chest pain listed as the first symptom 24 would have been considered more severe or important than shortness of breath which is listed as the second symptom 24 in input list 10.

In the present invention, a health care provider can actually type in the inputs 24 into input list 10 or the present invention may be configured so that a user can select the input 24 from selecting from a list of signs or symptoms. The present invention may also be configured so that as a user begins to input the first letter of a sign/symptom, then all signs/symptoms beginning with that same first letter will appear so that the user can select the sign/symptom instead of having to input the entire sign/symptom.

As a user inputs or selects inputs 24 in input list 10, the present invention may operate to isolate all potential diseases or conditions associated with each specific input 24. As illustrated in FIG. 2, in isolating all potential diseases or conditions associated with each specific input 24, the present invention may create a differential diagnosis data table 12. Differential diagnosis data table 12 is simply a data table illustrating the diseases or conditions associated with each specific input 24. Differential diagnosis data table 12 may be configured to include one or more sub-tables 14. Sub-tables 14 are data tables also known as the signs/symptoms/findings (SSF)-differential diagnosis (DD) sub-table 14 or the SSF-DD sub-table 14. SSF-DD sub-table 14 is a data table that includes a symptoms table list 22 for each particular input 24. Symptoms table list 22 includes a listing of one or more potential diseases or conditions 16 or differential diagnosis (DD) 16 that are associated with the particular input 24. In a preferred embodiment, the rank order of the differential diagnosis/potential diseases DD, such as the listing of potential DD entries 16 in symptoms table list 22 will be based on epidemiological distribution (disease prevalence) of the diseases in the general population.

Thus, the DD 16 in symptoms table list 22 is a potential differential diagnosis for the particular input 24. For Example, in FIG. 2, there are two inputs 24A—chest pain and 24B—shortness of breath; thus, there will be at least two SSF-DD sub-tables 14 for each particular input—one for chest pain 24A and one for shortness of breath 24B as illustrated in FIG. 2. And each SSF-DD sub-table 14 will include a symptoms table list 22 with a listing of one or more differential diagnosis (DD) 16 associated with particular inputs 24A and 24B. DD entries 16 are the actual diseases or conditions that are associated with the particular inputs 24A and 24B. Thus, the symptoms table list 22 for 24A—chest pain lists "Myocardial Ischemia" as the first DD entry 16 associated with the chest pain input 24A.

While FIG. 2 only illustrates ten DD entries 16 with each symptoms table list 22, the present invention is not limited to any particular number of DD entries 16 for any particular input 24. FIG. 2 also illustrates an output table 34 that may be output by the present invention. In one embodiment, the present invention is configured to generate output table 34 which is the actual output listing of diseases or conditions that are associated with the particular patient that is being interviewed or treated by a health care provider.

FIG. 2 also illustrates that output table 34 may include at least two lists: the ranked high probability differential diagnosis list 26 and the ranked low probability differential diagnosis list 28. Lists 26 and 28 illustrated in FIG. 2 are examples of lists that will be generated by the present invention. FIG. 2 illustrates the lists 26 and 28 before the lists have been fully populated with the potential DD entries 16.

Figure 3:
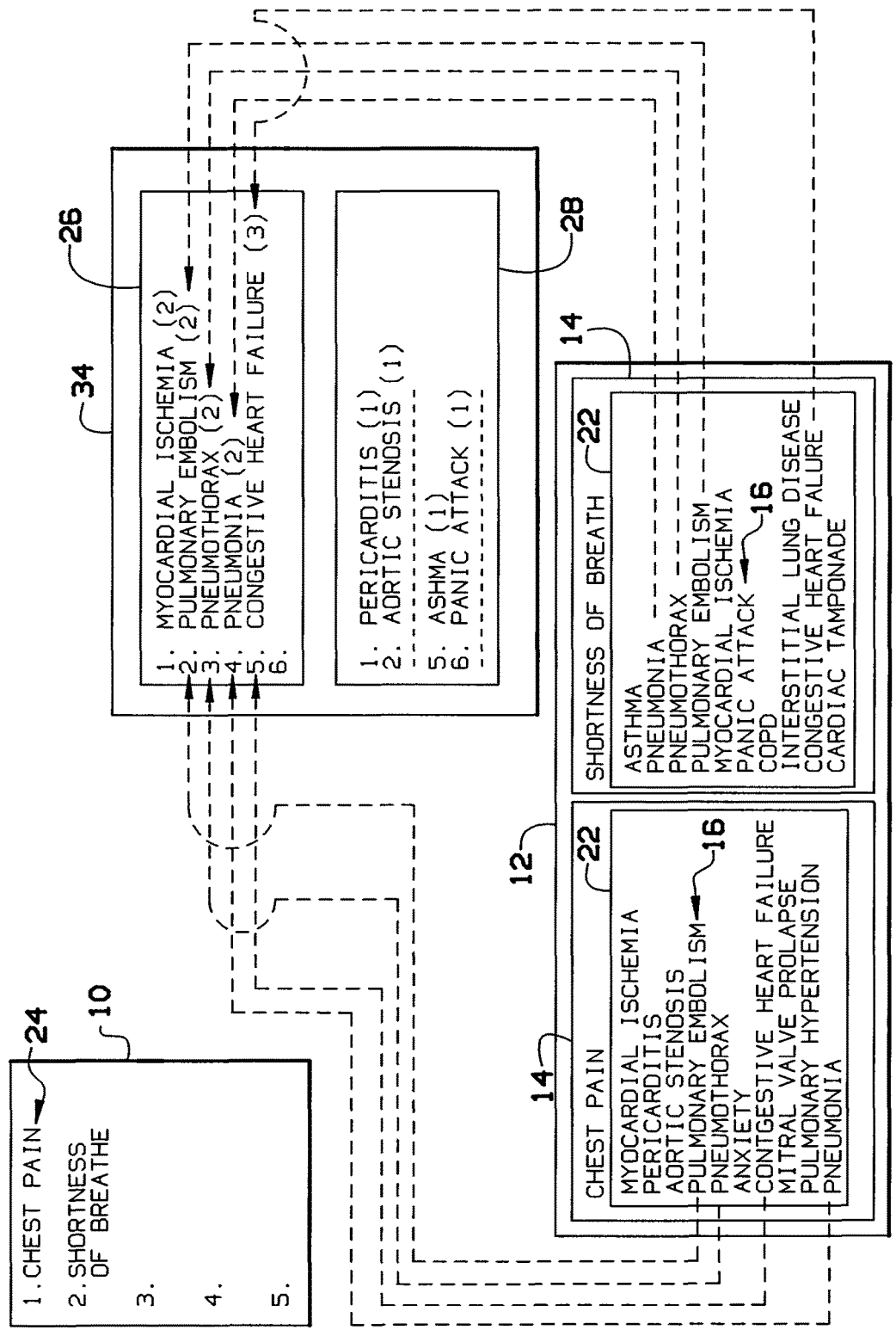
FIG. 3 illustrates another schematic exemplary view of an embodiment of the present invention demonstrating a differential diagnosis (DD) isolation.

FIG. 3 illustrates another schematic exemplary view of an embodiment of the present invention demonstrating a differential diagnosis (DD) isolation. FIG. 3 illustrates FIG. 2, but after the potential DD entries 16 have been extracted from symptoms table lists 22 and populated into the high probability differential diagnosis list 26 and the low probability differential diagnosis list 28. In FIG. 3, the high probability differential diagnosis list 26 has been populated with the potential DD entries 16 that have a high probability of being the disease or condition that a patient is suffering based upon the inputs 24 (24A—chest pain and 24B—shortness of breath) that have been input by the user/health care provider. The listing of potential DD entries 16 illustrated in lists 26 and 28 of FIG. 3 are in a non-rank sorted configuration and are merely the listing of high probability diseases for list 26 and low probability diseases for list 28. For example, list 26 would include the listing of high probability diseases associated with inputs 24A and 24B and list 28 would include the listing of low probability diseases associated with inputs 24A and 24B.

Figure 4:
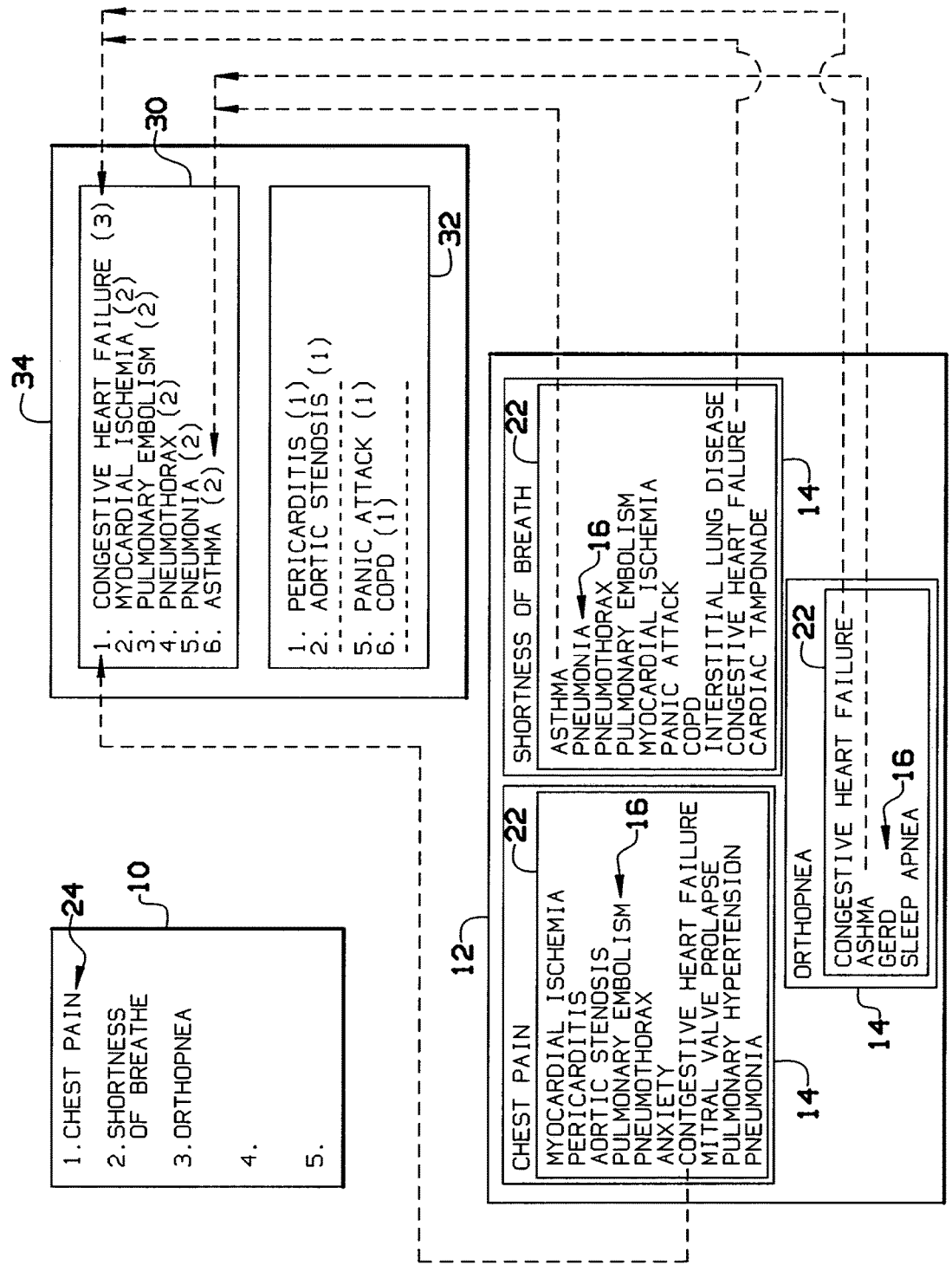
FIG. 4 illustrates is a schematic exemplary view of an embodiment of the present invention demonstrating high and low probability differential diagnosis.

FIG. 4 illustrates is a schematic exemplary view of an embodiment of the present invention demonstrating high and low probability differential diagnosis. FIG. 4 illustrates FIG. 3 after the present invention has analyzed the inputs 24, the symptoms table lists 22 and compared the symptoms tables lists 22 for the inputs 24 so that the present invention can rank the listing of high probability diseases for list 26 of FIG. 3 and rank the low probability diseases for list 28 of FIG. 3. In FIG. 4, the high probability differential diagnosis list 26 of FIG. 3 is illustrated by the ranked and sorted high probability differential diagnosis list 30. And the low probability differential diagnosis list 28 of FIG. 3 is illustrated by the ranked and sorted low probability differential diagnosis list 32. Thus, list 30 would include the ranked and sorted listing of high probability diseases associated with inputs 24A and 24B and list 32 would include the ranked and sorted listing of low probability diseases associated with inputs 24A and 24B.

In a preferred embodiment, ranked and sorted list 30 would be output to a user/health care provider to notify the health care provider of the listing of diseases that a patient has a high probability of having and also providing a user with ranked and sorted list 32 to notify the health care provider of the listing of diseases that a patient has a low probability of having.

The present invention may be configured to include a medical database of signs/symptoms/findings (SSF) and the diagnoses linked to these signs/symptoms/findings (SSF) which has been compiled from various medical resources. If a user enters any inputs 24 that are not included within such a medical database of SSF, then the new entry can be added to the medical database of SSF. Thus, a user is given the option to update the medical database in various situations, i.e. as new SSF/inputs are discovered or if a particular SSF/input is not included, and may also update the database to account for scenarios in which a particular SSF is within the database but may be listed/phrased in a particular manner that certain users may not recognize. For example, one user may list a particular input/SSF, such as "fever," as "fever" and another user may prefer to use a specific type of fever, such as "post-operative fever." If "post-operative fever" were not included within the present invention, then the user/health care provider may update the database by adding "post-operative fever" to the database. This listing/example of "fever" is for example purposes only and is not to be construed as a limitation of the present invention. In addition, due to various linguistic backgrounds, certain users/health care providers may refer to certain inputs/SSFs in one manner while users/health care providers with a different linguistic background may refer to the same inputs/SSFs in a different manner. In these situations, the users/health care providers may be given the opportunity to update the database to add inputs/SSFs to accommodate for different linguistic backgrounds. In addition, the present invention may be configured so that users/health care providers may update the diagnoses/diseases linked to the signs/symptoms/findings (SSF). For example, as new diagnoses are discovered and/or if new research were to indicate that certain signs/symptoms/findings are linked to certain diagnoses not within the medical database, then users/health care providers can update the database to contain said new diagnoses.

In one embodiment, the present invention will analyze the inputs 24 and the listing of potential DD entries 16 and further analyze which potential DD entries 16 are linked to the various inputs 24 to determine which potential DD entries 16 are common among and/or linked to the inputs 24.

By way of example, if a health care provider/user is entering and/or selecting inputs 24 which are present within the medical database of signs/symptoms/findings (SSF), the potential diseases, conditions, or differential diagnosis (DD) 16 have to be analyzed an placed in a rank order. Table 1 illustrated below illustrates potential diseases that are linked to various signs/symptoms/findings (SSF) or inputs 24 in FIGS. 2, 3, and 4. The letters utilized in Table 1 below are used for illustration purposes only whereby each letter represents a different potential disease.

TABLE 1

| Inputs/SSF | Potential Diseases/Differential Diagnoses (DD) |
| --- | --- |
| SSF1 | A, G, H, B, T, O, I, P, X, Y, Z |
| SSF2 | A, J, K, C, B, X, Q, R, S |
| SSF3 | C, U, L, N, X, T, W, V, S |

In one embodiment of the present invention, an output list of ranked and sorted high probability differential diagnosis, such as list 30 of FIG. 4 will be compiled and output based upon possible combinations of signs/symptoms/clinical and laboratory findings used in the analysis.

From Table 1, the possible combinations will include: (1) SSF1, SSF2, and SSF3; (2) SSF1 and SSF2; (3) SSF1 and SSF3; and (4) SSF2 and SSF3. An example for an analysis by an embodiment of the present invention based upon combination 1 (SSF1, SSF2, and SSF3) is as follows: a differential diagnosis (DD) (e.g., X) linked to input 3 (SSF3) is the same as the potential disease or differential diagnosis (DD) (e.g., X) linked to input 1 (SSF1) and the same as the potential disease or differential diagnosis (DD) (e.g., X) linked to input 2 (SSF2); thus, the specific potential disease or differential diagnosis DD (e.g., X) becomes ranked number one in the DD outcome section for high probability differential diagnosis because it is associated with three potential differential diagnosis (DD) and has a total weight of three associated with being linked to all three inputs (SSF1, SSF2, and SSF3). This DD (e.g., X) will be ranked ahead of other DD that are only associated with two SSF (repeated only twice). This is also based in part on the configuration in a preferred embodiment, whereby the rank order of the differential diagnosis/potential diseases DD, such as the listing of potential DD entries 16 in symptoms table list 22 is based on epidemiological distribution (disease prevalence) of the diseases in the general population.

An example for an analysis by an embodiment of the present invention based upon combination 2 (SSF1, and SSF2) is as follows: A differential diagnosis (DD) (e.g., A) linked to input 2 (SSF2) is the same as the potential disease or differential diagnosis (DD) (e.g., A) linked to input 1 (SSF1); thus, the specific potential disease or differential diagnosis DD (e.g., A) becomes ranked number two in the DD outcome section for high probability differential diagnosis (it was repeated twice). Thus, in this example, the specific disease or differential diagnosis (A) that was linked to input 1 (SSF1) and input 2 (SSF2) would be ranked number two, behind X from combination 1 in the ranked and sorted high probability differential diagnosis list 30 of FIG. 4.

A second example for an analysis by an embodiment of the present invention based upon combination 2 (SSF1, and SSF2) is as follows: A differential diagnosis (DD) (e.g., B) linked to input 2 (SSF2) is the same as the potential disease or differential diagnosis (DD) (e.g., B) linked to input 1 (SSF1). The potential disease or differential diagnosis DD (e.g., B) is located after DD (A) in the list of DD linked to input 1 (SSF1) and in the list of DD linked to input 2 (SSF2). Thus, in this example, the specific disease or differential diagnosis (B) that was linked to input 1 (SSF1) and input 2 (SSF2) would be ranked number three, behind A and X in the ranked and sorted high probability differential diagnosis list 30 of FIG. 4. This ranking is such because the present invention, in one embodiment, is configured to rank diagnoses based upon the priority in which a DD is located in the list of potential diseases or conditions, such as the listing 22 of FIGS. 2 and 3 of one or more potential diseases or conditions 16 of FIGS. 2 and 3, because the listing of potential diseases is based on epidemiological distribution (disease prevalence).

An example for an analysis by an embodiment of the present invention based upon combination 3 (SSF1 and SSF3) is as follows: A differential diagnosis (DD) (e.g., T) linked to input 1 (SSF1) is the same as the potential disease or differential diagnosis (DD) (e.g., T) for input 3 (SSF3); thus, the specific potential disease or differential diagnosis DD (e.g., T) becomes ranked number four in in the DD outcome section for high probability differential diagnosis. The present invention can rank this differential diagnosis DD (e.g., T) as number four by looking at the chronology of the DD (e.g., T) linked to input 1 (SSF1). From Table 1, DDs, X, A, and B, are ranked ahead of DD (e.g., T) because X is linked to all three inputs (SSF1, SSF2, and SSF3) and is ranked first with A and B ranked second and third, leaving T to be ranked fourth.

In other embodiments, A and B will also be ranked ahead of T based upon the methodology that inputs (SSF) are selected and/or input by users/health care providers in order of severity or importance such that diseases associated with the more important input, SSF1, will be ranked ahead of diseases associated with less severe inputs, such as SSF3. By way of example, DD (e.g., A) is ranked ahead of DD (e.g., T) because DD (e.g., A) is linked to SSF1 and SSF2 while DD (e.g., T) is linked to SSF1 and SSF3. A and B are also ranked ahead of T in this particular example because both A and B are ranked ahead of T in the list of Potential diseases/differential diagnoses linked to input 1, SSF1, illustrated in Table 1. In a preferred embodiment, the present invention will be configured so that the diagnoses/diseases in the ranked and sorted high probability differential diagnosis list, such as list 30 of FIG. 4, will be ranked based upon the order of the potential diseases/diagnoses linked to the first input (e.g., the diseases linked to SSF1) in addition to number of times a particular disease/diagnosis is also linked to other inputs (SSFs) as illustrated in the analysis herein based upon Table 1. However, when a particular potential disease/diagnosis (e.g., A of Table 1) is found to be linked to the same number of symptoms (SSFs) as another potential disease/diagnosis (e.g., B of Table 1), then the order that the particular disease/diagnosis is ranked within the list of potential diseases/diagnosis, such as the order within symptoms table list 22 of FIGS. 2, 3, and 4, will take precedence and be ranked ahead of the other potential disease in the ranked and sorted high probability differential diagnosis list, such as list 30 of FIG. 4. Thus, A is ranked ahead of B. This ranking is premised upon the principle that the listing of diseases within the lists, such as list 22, are based upon epidemiological distribution (disease prevalence).

When the present invention performs analysis and ranking functions, if any DD stands higher in the list for input 1 (for example A stands higher than T), that specific DD takes its place as rank 1 (higher rank) as compared to the other DD (which takes its rank in the second position). Subsequently, after rankings regarding links to input 1, then rankings will be based upon links to input 2. Thus, if any DD stands higher in the list for input 2 (for example, J stands higher than K), that specific DD takes the next rank and so on.

An example for an analysis by an embodiment of the present invention based upon combination 4 (SSF2 and SSF3): A differential diagnosis (DD) (e.g., C) linked to input 3 (SSF3) is the same as the potential disease or differential diagnosis (DD) (e.g., C) for input 2 (SSF2); thus, the specific potential disease or differential diagnosis DD (e.g., C) becomes ranked number five in in the DD outcome section for high probability differential diagnosis. Here priority is given to the DDs linked to input 1 (SSF1) over the DD linked to input 2 (SSF2).

The present invention may also be configured to choose between the DD that are linked to the same number of symptoms (SSFs). Again, the DDs that are linked to the greatest number of symptoms (SSFs) will be ranked ahead of those DDs that are linked to a lower number of symptoms (SSFs). For example, differential diagnosis X of Table 1 will be ranked ahead of differential diagnosis A because differential diagnosis X is linked to three symptoms (SSF1, SSF2, and SSF3) and differential diagnosis A is only linked to two symptoms (SSF1 and SSF2). Embodiments of the present invention can be configured to rank those differential diagnoses that are all linked to the same number of symptoms (SSFs) in an order amongst themselves (those DDs all linked to same number of symptoms) by reviewing and analyzing the chronology of the DDs linked to a particular input, such as input 1 (SSF1). Thus, for those DDs with an equal number or input linkings, the present invention can rank those based upon the order in which the particular DD is ranked for an input, such as input 1 (SSF1); thus, all DDs linked to two inputs (SSFs) one of which is SSF1—i.e. A, B, and T, the specific DDs that stand higher in the list of DDs linked to SSF1 will be ranked higher in the DD outcome section as compared to other DDs which stand lower in the list for input 1 (SSF1). For example, in looking at the table above, differential diagnosis/potential disease A stands in a higher position than differential diagnosis/potential disease B, and therefore differential diagnosis/potential disease A will be ranked higher than differential diagnosis/potential disease A.

In some embodiments, the present invention may also be configured to allow a user/health care provider to search records for any specific differential diagnosis or potential disease and obtain a list of all the signs, symptoms and findings that are linked to a specific differential diagnosis DD or disease. For example, utilizing Table 1, a user can search for differential diagnosis DD or potential disease A, and the present invention can provide the user with SSF1 and SSF2, which are the symptoms associated with the differential diagnosis DD or potential disease A. Providing this information will assist a user by providing a user with a system that can remind the user of the particular symptoms associated with particular inputs or signs/symptoms/findings SSFs.

Using Bayes' theorem, the maximum possible probability for any disease is 99%, not 100%. This is because the denominator of Bayes' theorem is always higher than the numerator. Thus, a maximum possible value is 0.99. So, even a probability of 99% means that 1 out of 100 patients with the exact same findings will not have the disease diagnosed, even though the presenting signs and symptoms look exactly like that disease. Thus, one should consider multiple differential diagnoses during any clinical encounter. Embodiments of the present invention will account for the possibilities that some patients will not have the disease/ diagnosis that is diagnosed as the high probability differential diagnosis. By analyzing multiple symptoms (SSFs) and providing multiple high probability differential diagnoses and also providing a listing of low probability differential diagnoses, the present invention accounts for the possibility that the patient will not have the diagnosed disease or at least one of diseases output in the lists in that the user/health care provider is provided with a list of potential diseases so that the user/health care provider can account for the fact that at least 1 out of 100 patients will not have the diagnosed disease.

According to Ockham's razor, if multiple competing theories are used to explain a fixed set of given facts, in general the theory using the least number of assumptions is given the highest credence. In diagnostic decision making, this principle means finding the fewest diagnoses that explain the most signs and symptoms. The present invention will perform its analysis of signs/symptoms/findings and compare the diseases linked to each of the signs/symptoms/ findings to provide a high probability differential diagnosis output that rank orders the potential diseases that a patient may have. Thus, the present invention is configured to provide a user with the fewest diagnoses that are linked to the most signs/symptoms/findings by providing the high probability differential diagnosis output.

Health care providers may experience clinical scenarios where a unifying diagnosis (diagnosis that explains all signs, symptoms and findings) is not available. The present invention helps in that it will generate a high probability differential diagnosis output whereby most of the signs, symptoms and findings get the highest preference. According to the Bayes' theorem, it is not possible to attain 100% certainty for any given diagnosis and possibility of alternative diagnoses always exists. So it is safer to consider multiple differential diagnoses at any given time during clinical problem solving. The present invention will satisfy this rule in that embodiments of the present invention will consider all possible combinations for the available signs, symptoms and clinical findings to generate a high probability differential diagnosis. The present invention may also be configured to add up the total number of signs and symptoms that is explained by each of the differential diagnoses, and then identify the differential diagnosis that has the highest number of signs and symptoms and clinical findings for the user/health care provider so that the user/health care provider may utilize that information during the patient interview or during treatment.

The present invention may also be configured to follow epidemiologic distribution of diseases to rank order the differential diagnoses. A universal weight of 1 may be assigned to differential diagnoses linked to signs, symptoms or findings, and a higher weight may be assigned for any differential diagnoses that are life threatening, very common in a given population, and the present invention may also be configured to use age, sex, or epidemiological distribution of disease to rank order the differential diagnoses.

For example, in one embodiment, a specific weight can be assigned to each sign, symptom or finding during diagnostic decision making. In the present invention, to satisfy the rule of addition, a universal weight of one (1) is assigned to any sign and symptom or finding during generating the high priority differential diagnoses. The present invention may also be configured to use one to many relationships with signs, symptoms, or findings. In some embodiments, the present invention may be used to assign higher rank to those differential diagnoses that are common among the signs, symptoms and clinical findings. In addition, the present invention may also be configured to assign a unique name for the same disease throughout the database. Thus, the present invention may be configured to understand and utilize the simplest form of Ockham's razor and Bayes theorem in generating the high probability differential diagnosis output.

The present invention may also be configured to treat life threatening differential diagnoses differently by assigning higher weights compared to other diagnoses. Instead of assigning a universal weight of 1 for a potential disease or differential diagnosis, the present invention may assign a weight of 2 to potential life threatening diseases or differential diagnoses. In assigning the greater weights of 2, or other value, any differential diagnoses including the higher weighted life threatening diseases will take the highest place or be ranked higher in the ranked and sorted high probability differential diagnosis list 30 of FIG. 4.

In alternative embodiments, the present invention may also assign a higher weight to potential diseases or differential diagnoses that are highly prevalent in a certain group of population so that the corresponding diagnosis is ranked higher among other high probability differential diagnoses that may not be as prevalent in the certain group of population.

Some embodiments may also be configured so that rare differential diagnoses are treated differently. In particular, rare diseases may be assigned smaller weights, such as a weight value of 0.5, so that rare diseases will be ranked in the lowest of lists for such rare disease diagnoses. Thus, rare diseases may appear ranked in the bottom of the ranked and sorted low probability differential diagnosis list 32 of FIG. 4. Thus, while the rare diseases likely will not appear in the high probability differential diagnosis list, the rare diseases can be presented to a user/health care provider so that the user/health care provider will be made aware of the potential rare diseases associated with the particular signs/symptoms/findings a patient is experiencing.

The present invention will also generate low probability (less likely) differential diagnoses by accumulating all the non-repeated differential diagnoses which are linked to the sign, symptoms and findings used in the search. An embodiment may be configured to output a ranked and sorted low probability differential diagnosis list 32, as illustrated in FIG. 4. These are the diseases which are possible to present in rare situation. Thus, a user/health care provider can rule out all the available high probability differential diagnoses, and can then review the ranked and sorted low probability differential diagnosis list 32 to find a diagnosis when treating a patient.

In addition, the present invention may be configured so that users will be able to find all the signs, symptoms and findings linked to a specific differential diagnoses or disease by utilizing a reverse search strategy (instead of using signs, symptoms and findings to generate differential diagnoses, a user can search diseases to find signs, symptoms and findings). This search function will be linked to each and every differential diagnoses generated (high or low probability) to help remind and inform users of other information needed to complete a diagnostic testing or loop when evaluating a patient.

Figure 5:
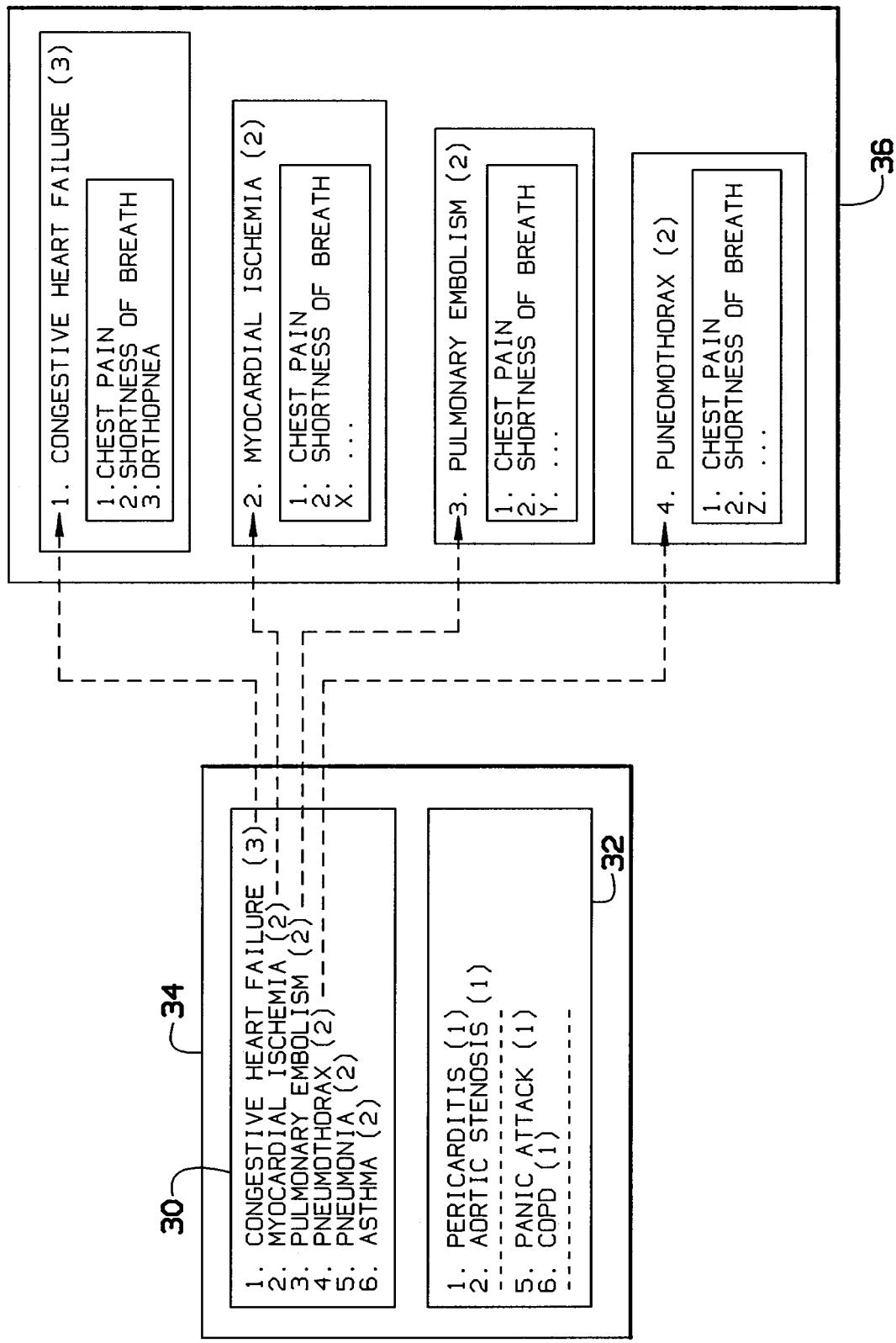
FIG. 5 is a schematic exemplary view of an embodiment of the present invention demonstrating reverse search technique where linked signs, symptoms, clinical and laboratory findings are shown.

FIG. 5 is a schematic exemplary view of an embodiment of the present invention demonstrating the reverse search technique where a user can search a disease and obtain all of the linked signs, symptoms, and laboratory findings associated with the searched disease. Illustrated in FIG. 5 is output table 34 including ranked and sorted high probability differential diagnosis list 30 and ranked and sorted low probability differential diagnosis list 32. In the present invention, a user/health care provider could search for a disease, such as congestive heart failure, as illustrated within list 30 of FIG. 5. In searching congestive heart failure, the present invention can provide a user with an illustration of the signs/symptoms/findings associated with congestive heart failure. For example, as illustrated in FIG. 5, in searching any number of diseases, such as congestive heart failure or any of the diseases illustrated in list 30 of FIG. 5, the present invention can produce a findings list 36 which lists the signs/symptoms/findings associated with the diseases that a user searched. Thus, findings list 36 illustrates the signs/symptoms/findings from the differential diagnosis data table 12 of FIG. 4. Thus, by performing a reverse search, the present invention will analyze the disease searched, such as congestive heart failure, and then provide the user with findings list 36 that lists of signs/symptoms/findings associated with congestive heart failure. In providing a reverse search capability, the present invention assists users in verifying its analysis and to assist with the patient interview in completing a diagnostic review of the patient.

In one embodiment, the present invention may also be configured to provide a user with additional information regarding the output table 34 including ranked and sorted high probability differential diagnosis list 30 and ranked and sorted low probability differential diagnosis list 32. For instance, the present invention may be configured to provide a user with other signs, symptoms and clinical findings linked to a generated differential diagnosis and provide a user with treatment strategies, disease management protocols, and other related information associated with the differential diagnoses lists, 30 and 32, contained within output table 34. Thus, once the present invention has generated a high probability differential diagnosis list of potential diseases for a patient, the user can then obtain treatment measures and strategies for treating the various diseases. These strategies may include treatment medicines, tests to be ordered, and the like.

Elements that could be added to the present invention in alternative embodiments include integrating with electronic medical records (history and physical examination, progress notes or assessments or lists of presenting signs, symptoms, clinical findings, or the like) in a fashion that could find a patient's presenting sign or symptoms, or clinical findings (by utilizing a search engine) and then generate the high probability differential diagnoses. The health care provider would be able to see reminders for those differential diagnoses during their subsequent electronic medical record review. This could work as a health care provider reminder system and might help to prevent diagnostic error.

Figure 6A:
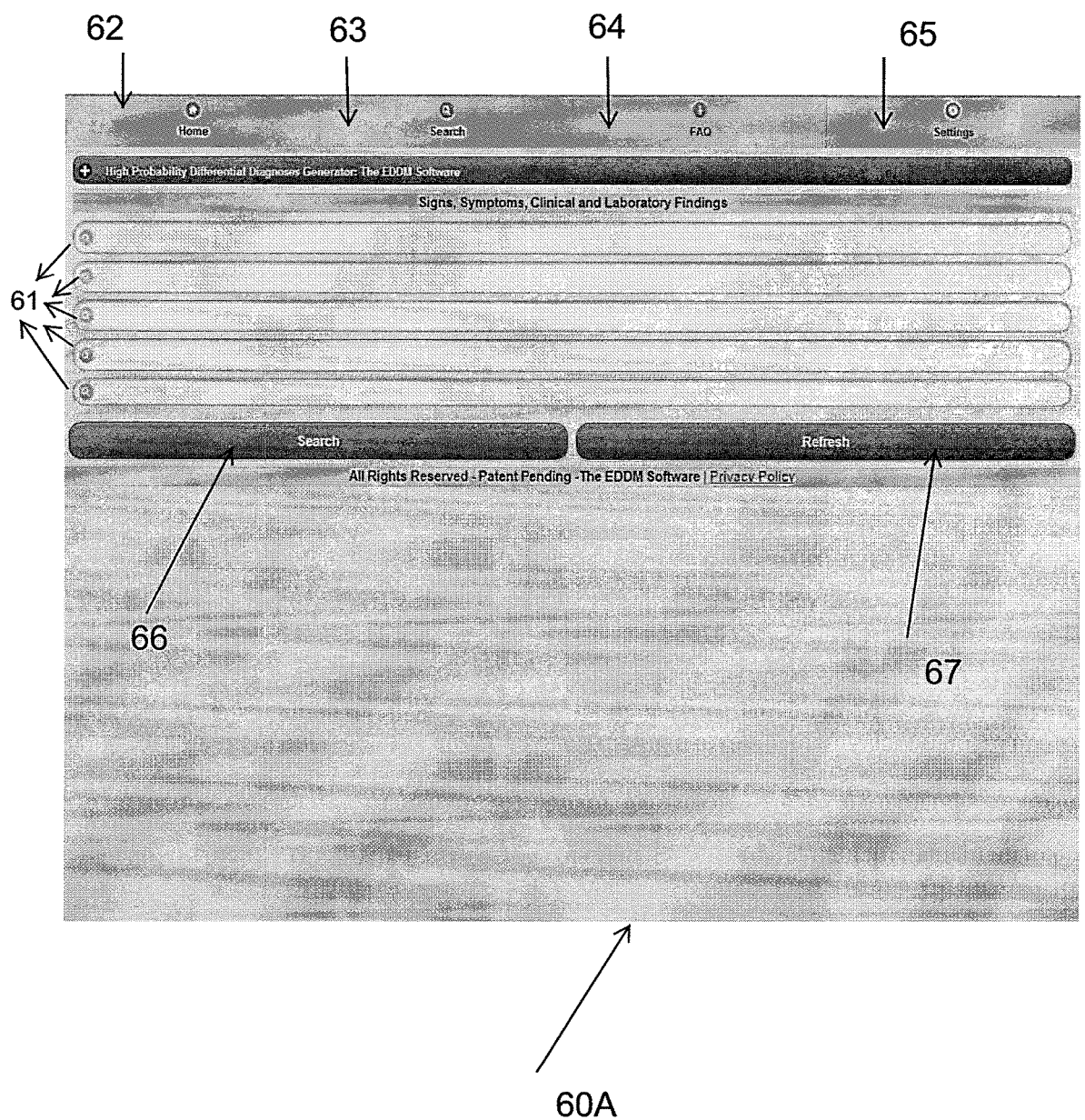
FIGS. 6A-6C illustrate screen shots of an embodiment of the present invention.
Figure 6B:
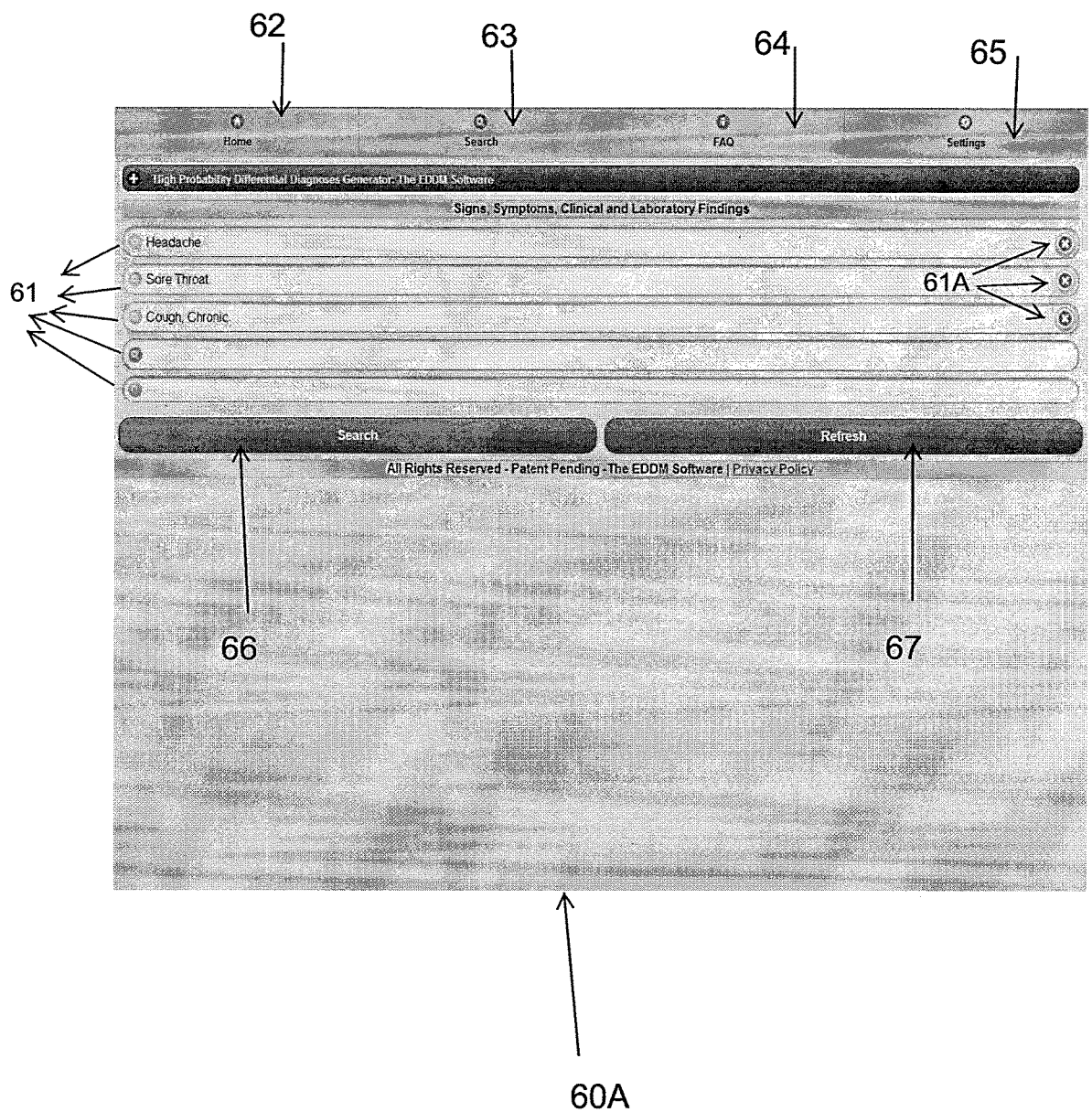
Figure 6C:
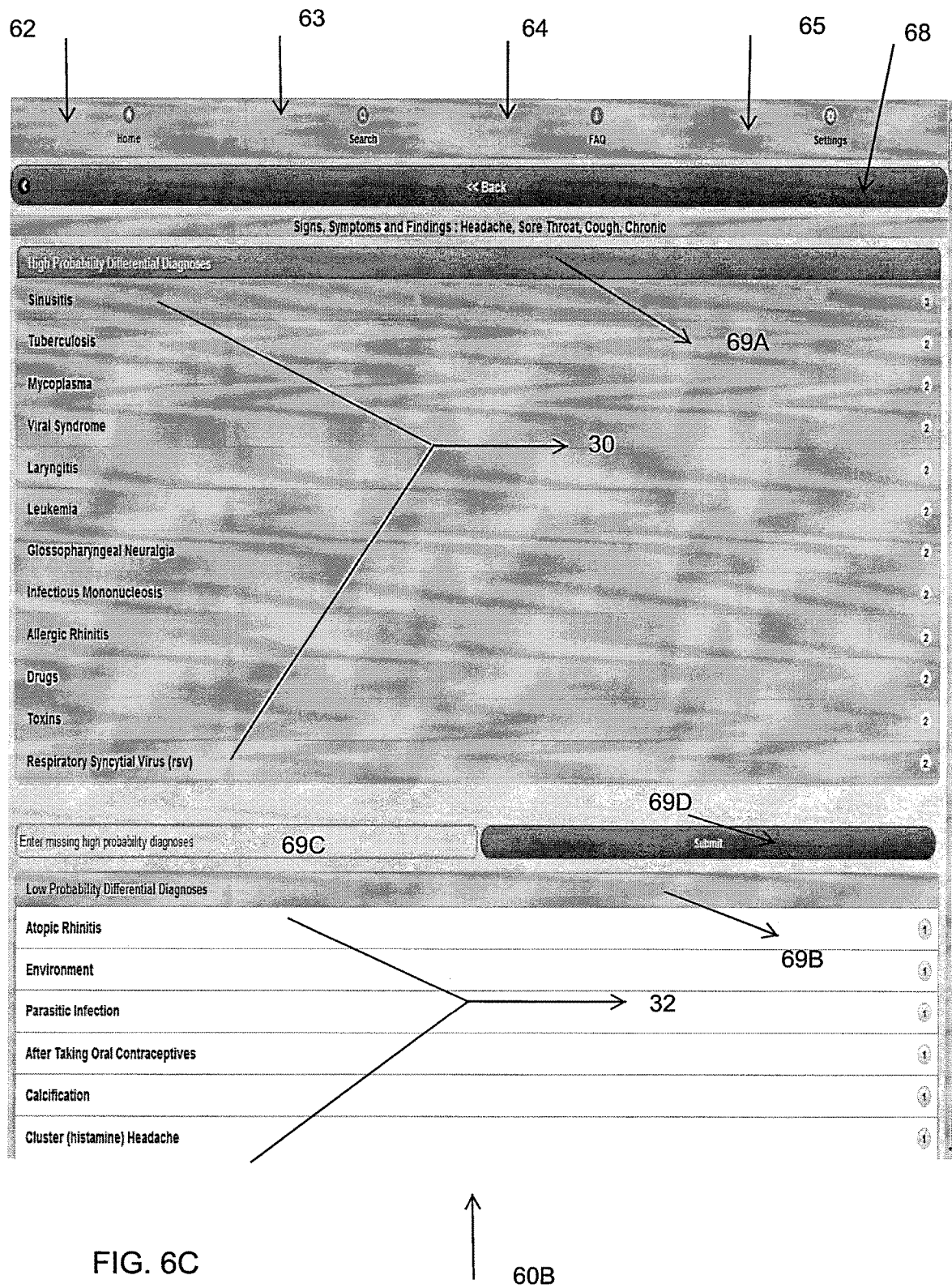

FIGS. 6A-6C illustrate sample screen shots of an example operation performed by one embodiment of the present invention. The screenshots are implemented in the THE DDXRX SOFTWARE input-disease-differential-diagnoses-output environment. It should be noted that the present invention is not limited by its application to the embodiment illustrated by THE DDXRX SOFTWARE.

FIGS. 6A and 6B illustrate window 60A. Window 60A illustrates input/selection drop down boxes 61, home selector 62, search selector 63, FAQ (frequently asked questions) selector 64, settings selector 65, search selector 66, and refresh selector 67. Input/selection drop down boxes 61 provides a manner in which a user can input/select a sign/symptom/clinical finding (SSF) that a patient is experiencing from a medical database of various signs/symptoms/clinical findings, such as headache, sore throat, chronic cough, chest pain, shortness of breath, orthopnea, etcetera. The present invention is not limited to this list as any number of symptoms may be available for a user to select.

Home selector 62 is a manner in which a user can get to a Home screen or may obtain help about the present window. For example, if a new user wanted information about the software, the user could activate the home selector to obtain such information; in addition, if a user were not sure how to input/select a symptom, the user could activate the home selector to obtain access to a help screen. Search selector 63 is a manner in which a user can obtain access to a window 60A to begin a new search/analysis of symptoms. From any screen, a user may be able to activate search selector 63 and the user may be returned to a blank search screen, such as window 60A of FIG. 6A to begin a new analysis/search based upon the selection of symptoms.

FAQ (frequently asked questions) selector 64 is a manner in which a user can get to a list of frequently asked questions about the present invention. For instance, the user can activate selector 64 which can then present a new window to a user that contains a list of frequently asked questions with answers to those questions for the benefit of the user. Settings selector 65 is a manner in which a user can change various settings about the present embodiment. For instance if the user wanted to change the layout, the size of text, or to review his/her login and password or change the password, the user could activate settings selector 65 to be brought to another window so that the user could carry out these functions.

Search selector 66 is a means in which a user can activate a search for a ranked high probability differential diagnosis list and a ranked low probability differential diagnosis list based upon the various inputs that are selected/input with input/selection drop down boxes 61. A user can activate search selector 66 and the user will be directed to window 60B of FIG. 6C. Refresh selector 67 provides a manner in which a user is able to clear the list of any inputs that are selected/input with input/selection drop down boxes 61 so that user may begin a new search. The lists of functions/actions set forth herein with respect to the various selectors are illustrative and do not limit the scope of the present invention.

FIG. 6B illustrates window 60 in which a user has selected/input some inputs with input/selection drop down boxes 61. Once a user has selected some symptoms (SSF) with boxes 61, the present invention may illustrate delete selectors 61A shown for each of input/selection drop down boxes 61 in which an input has been selected or input by a user. For example, in FIG. 6B, a user has input/selected three symptoms (SSFs)—headache, sore throat, and chronic cough. The user is now give the ability to delete any of those symptoms (SSFs) by activating delete selectors 61A. Thus, if a user wanted to delete the symptom sore throat, the user can activate delete box 61A next to the box illustrating sore throat. If a user wanted to delete all of the symptoms (SSFs) selected/input by a user, then the user can activate refresh selector 67.

FIG. 6C illustrates window 60B that is displayed after a user has entered/selected symptoms (SSFs) in boxes 61 and then activated search selector 66 of window 60A. Window 60B illustrates sub-window 69A, sub-window 69B, input box 69C, and submit selector 69D. Sub-window 69A displays the list of ranked and sorted high probability differential diagnosis, such as list 30 of FIG. 4. Sub-window 69B displays the list of ranked and sorted low probability differential diagnosis, such as list 32 of FIG. 4. Thus, after a user has input/selected various signs/symptoms (SSFs) in boxes 61 and activated search selector 66, the user is provided with the high probability differential diagnoses in sub-window 69A and the low probability differential diagnoses is sub-window 69B.

Input box 69C of window 60B is a manner in which a user can input any high probability diagnoses that the user/health care provider believes is missing from the list illustrated in sub-window 69A. After a user has input an diagnoses that is believed to be missing, a user can activate submit selector 69D to update the medical database to account for the missing diagnoses that should be associated with the inputs selected/input in boxes 61. The windows and illustrations in FIGS. 6A-6C regarding THE DDXRX SOFTWARE are for illustrative purposes and the present invention is not limited by its application to the embodiment illustrated by The DDxRx Software.

Figure 7:
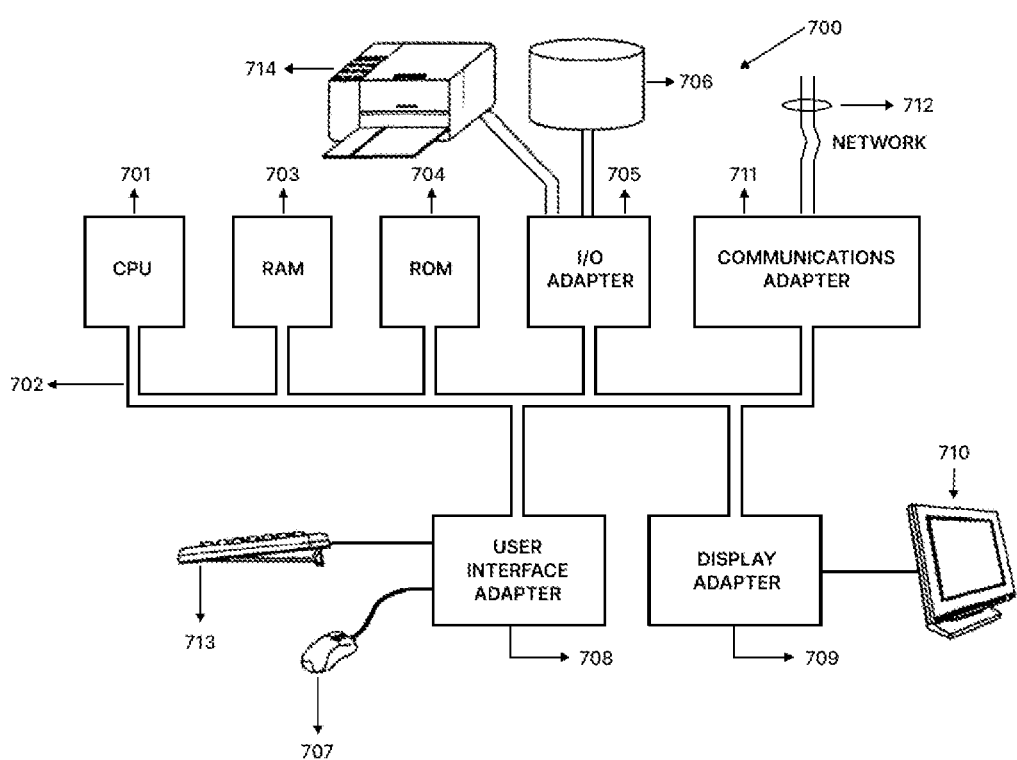
FIG. 7 depicts a block diagram of a computer system which is adapted to use an embodiment of the present invention.

FIG. 7 illustrates computer system 700 adapted to use embodiments of the present invention, e.g. storing and/or executing software associated with the embodiments. Central processing unit (CPU) 701 is coupled to system bus 702. The CPU 701 may be any general purpose CPU. However, embodiments of the present invention are not restricted by the architecture of CPU 701 as long as CPU 701 supports the inventive operations as described herein. Bus 702 is coupled to random access memory (RAM) 703, which may be SRAM, DRAM, or SDRAM. ROM 704 is also coupled to bus 702, which may be PROM, EPROM, or EEPROM. RAM 703 and ROM 704 hold user and system data and programs as is well known in the art.

Bus 702 is also coupled to input/output (I/O) controller card 705, communications adapter card 711, user interface card 708, and display card 709. The I/O adapter card 705 connects storage devices 706, such as one or more of a hard drive, a CD drive, a floppy disk drive, a tape drive, to computer system 700. The I/O adapter 705 is also connected to printer 714, which would allow the system to print paper copies of information such as documents, photographs, articles, etcetera. Note that the printer may be a printer (e.g. dot matrix, laser, etcetera), a fax machine, scanner, or a copier machine. Communications card 711 is adapted to couple the computer system 700 to a network 712, which may be one or more of a telephone network, a local (LAN) and/or a wide-area (WAN) network, an Ethernet network, and/or the Internet network. User interface card 708 couples user input devices, such as keyboard 713, pointing device 707, etcetera to the computer system 700. The display card 709 is driven by CPU 701 to control the display on display device 710.

In one embodiment, once the present invention has generated a high probability differential diagnosis list of potential diseases for a patient, as illustrated in FIG. 6C by the list of ranked and sorted high probability differential diagnosis, such as list 30, the user can then obtain treatment measures and strategies for treating the various diseases. In one embodiment, a user can click on any one of the diseases listed in list 30 to obtain treatment data.

Figure 8A:
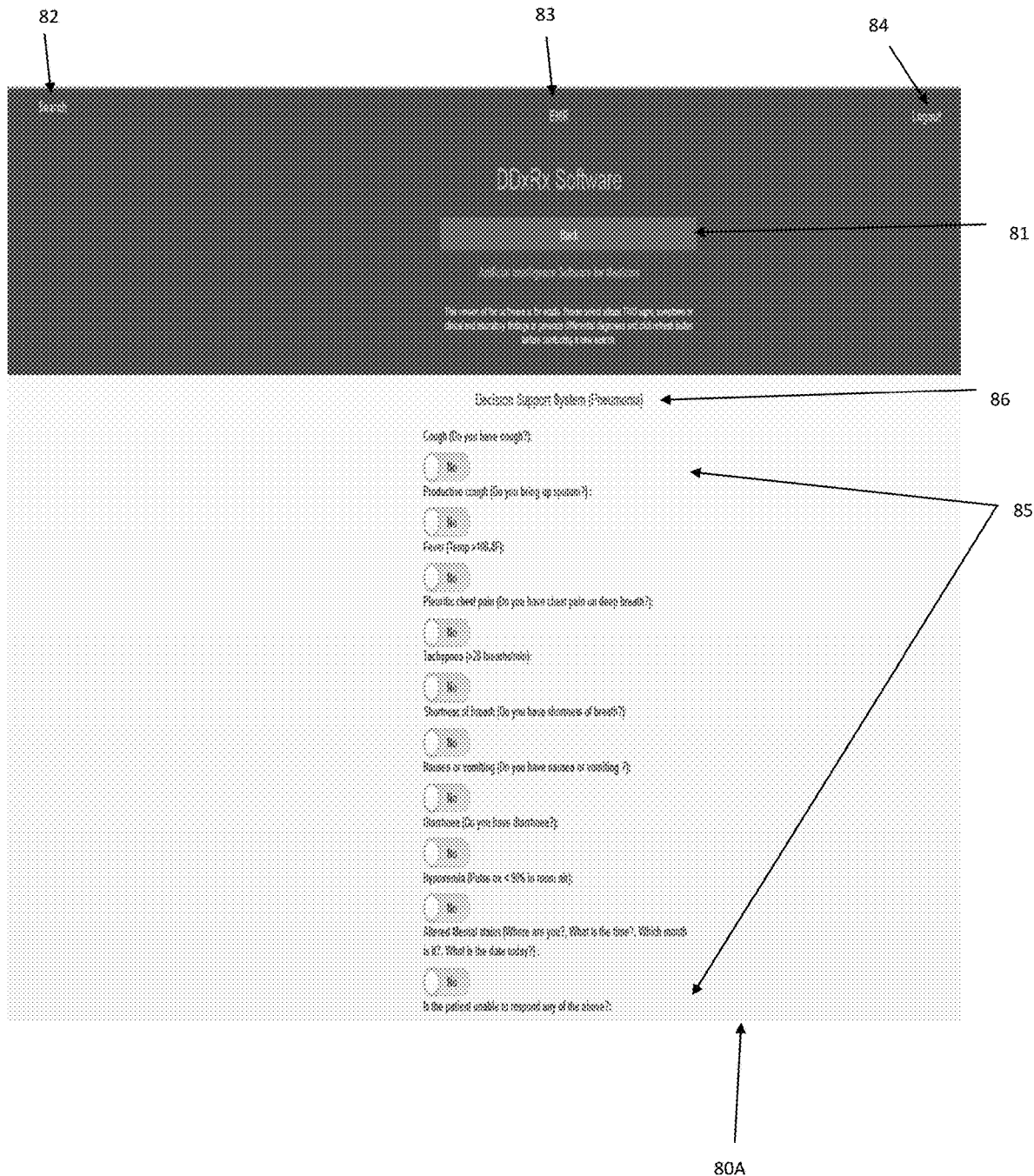
FIGS. 8A-8D illustrate screen shots of an embodiment of the present invention.
Figure 8B:
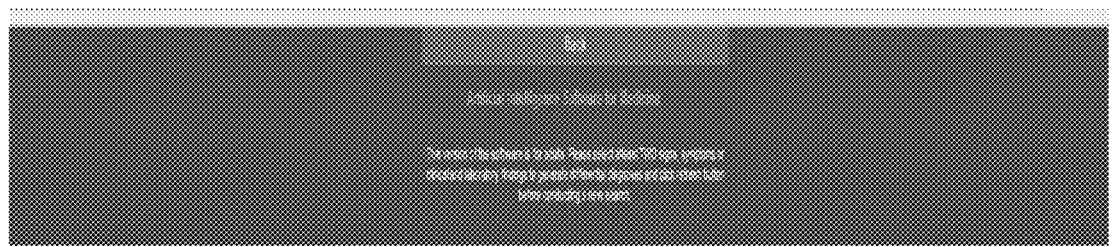

FIGS. 8A-8B illustrate sample screen shots of an example operation performed by one embodiment of the present invention. The present invention is not limited by its application to the screenshots illustrated by FIGS. 8A-8B. FIG. 8A illustrates a sample screen shot of an example operation performed by one embodiment of the present invention. Window 80A is displayed after a user has selected a disease in list 30. Window 80A illustrates back selector 81, search selector 82, EMR selector 83, logout selector 84, and diagnosis questions selectors 85. Back selector 81 provides a user with the ability to go back to the previous screen, such as window 60B in FIG. 6C so that a user can get back to list 30. However in alternative embodiments, the present invention may be configured so that back selector 81 is configured to get a user back to another screen of the present inventions such as window 60A. Search selector 82 provides a user with the ability to get back to window 60A of FIG. 6B so that a user can see the previously selected inputs that were selected with input/selection drop down boxes 61. At this point, the user can then proceed from window 60A to continue the examination by choosing additional or different inputs. In other embodiments, search selector 82 may direct a user back to window 60B of FIG. 6C so that user may select a different disease from list 30.

Figure 8C:
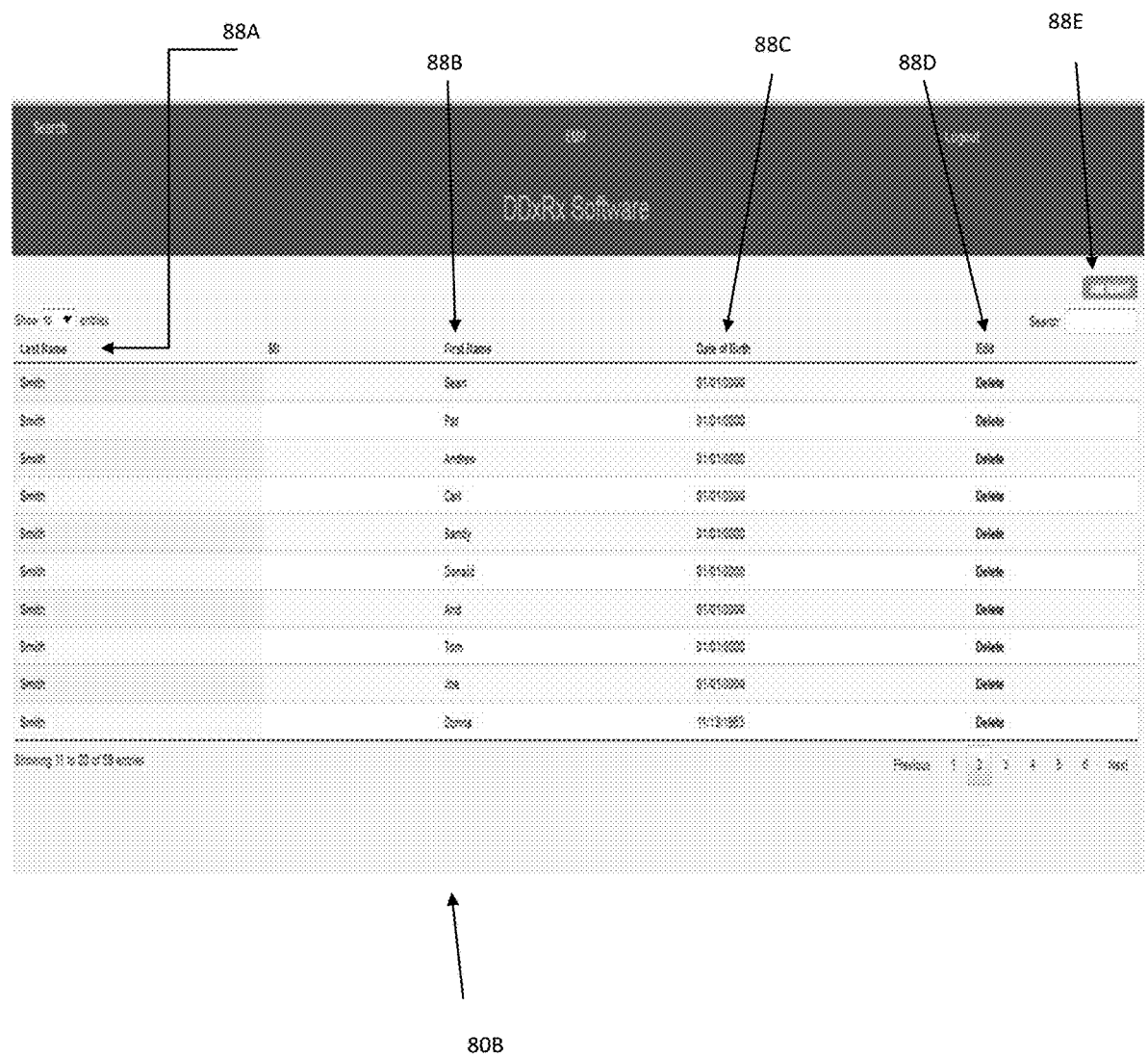
Figure 8D:
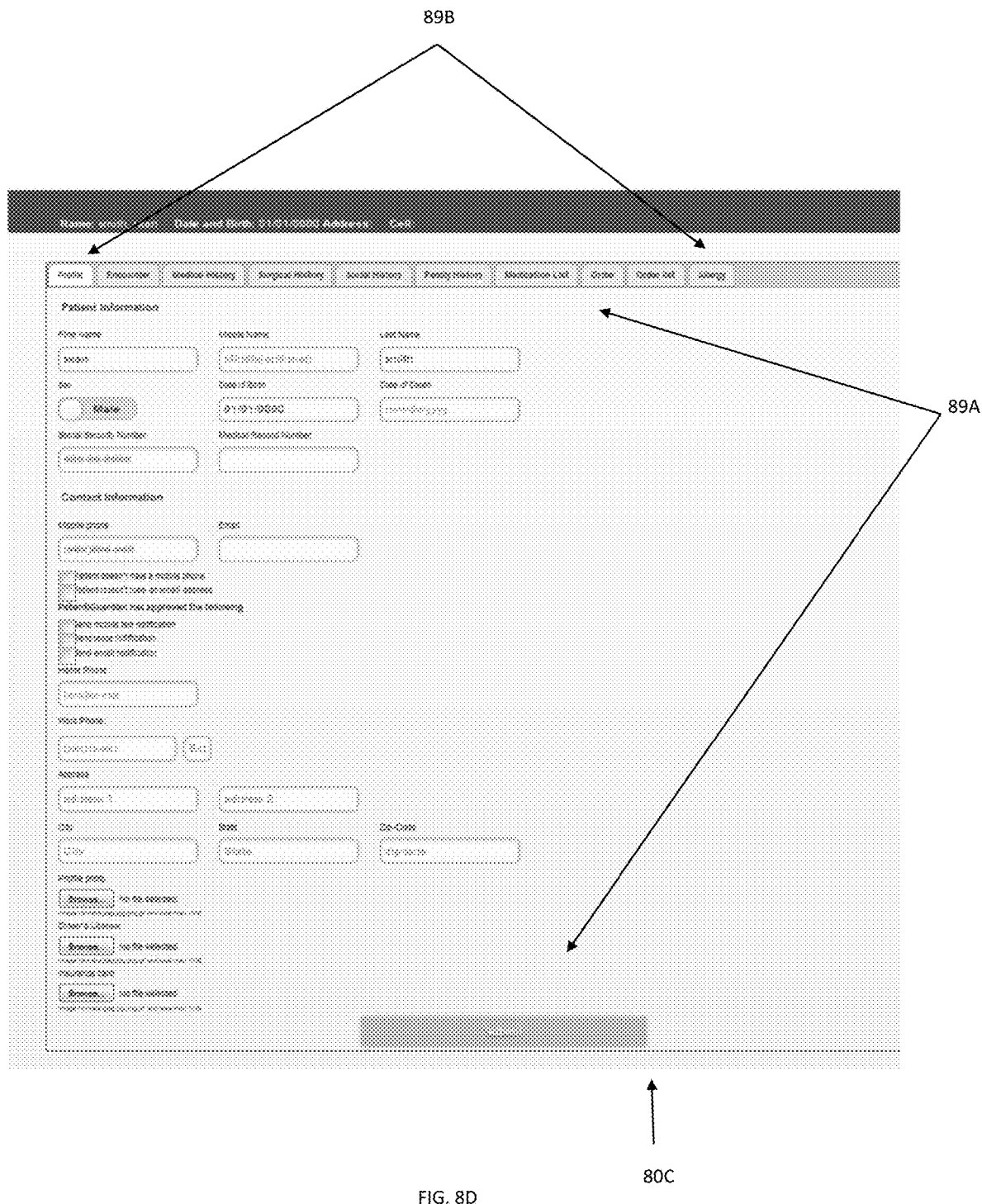

EMR (electronic medical record) selector 83 provides a user with the ability to access a patient's electronic medical record or an electronic medical record system so that a user can access a patient's electronic medical records. The present invention may be configured so that the present invention also stores and maintains a patient's electronic medical record. In one embodiment, when a user activates EMR selector 83, a user may be brought to window 80B illustrated in FIG. 8C. Window 80B and 80C in FIGS. 8C and 8D are sample screen shots of an example operation performed by one embodiment of the present invention. Window 80B of FIG. 8C, illustrates a list of patients from a medical database of records. These records may be stored in-house at the user's location, such as at a physician's office or at a hospital, or may be stored with a third party database that stores data for the user of the present invention. The list of patients may be configured to illustrate data for patients by various data fields, such as last name field 88A, first name field 88B, and date of birth field 88C. Thus, when looking at window 80B, a user can easily locate a patient by any of these fields. A user is also given the ability to edit a record by selecting edit field 88D. A user is also able to delete a record by choosing the edit field 88D for a particular patient. The present invention may also be configured to sort the data by selecting any of the data fields, such as last name field 88A, first name field 88B, and date of birth field 88C. By selecting a data field, the data may be sorted by that particular field. For example, when last name data field 88A is selected, the records will be sorted by last name.

The present invention may also be configured so that a user is able to create a new medical record for a patient, who may not be in the database of records, by selecting Add Patient selector 88E. By selecting Add Patient selector 88E, a user is then able to enter data to start a medical record for a new patient. The present invention may be configured so that when a patient is undergoing examination, a medical technologists, nurse or other health care professional can enter the information to create a medical record for a patient so that a physician's time is not wasted creating a medical record. Thus, by the time a physician sees a patient, the medical record is created.

In one embodiment, once a user finds the patient he is examining in the database of medical records, he can click on that patient's name and may be brought to window 80C illustrated in FIG. 8D. Window 80C illustrates the patient's electronic medical record to a user. Patient information block 89A of window 80C illustrates the various fields contained with the patient's medical record which corresponds to the data tabs 89B illustrated above information block 89A. In one embodiment of the present invention, the electronic medical record includes various types of data such as, profile data, encounter data, medical history data, surgical history, social history, family history, medication list, order data, order list data, and allergy data—as illustrated by the various data tabs 89B. The present invention is not limited to the data illustrated in FIG. 8D, as any number of different types of data may be included in a patient's electronic medical record. In one embodiment, the medical record may be configured so that various data stored in a patient's medical record is stored in a format so that the data may be automatically utilized during the diagnosis process. For example, a patient's age in his/her medical record may be stored in a certain format so that when a user is utilizing the present invention to diagnose a patient, the present invention will gather the patient's age from the medical record and make that data available during the diagnosis process so that when a user/physician is in the process of diagnosing a patient, the user/physician already has the patient's age to consider in the diagnosis process. In addition to age, the present invention may also gather and use any data from the patient's medical record and utilize that data during diagnosis, such as weight, medical history, surgical history and the like.

The present invention may also be configured so that when a user/physician is reviewing data in a patient's medical record, the user/physician can jump directly from the patient's medical record to window 60A of FIG. 6A to start the diagnosis process. In such an embodiment, an action tab or button may be located in the medical record tab anywhere in the medical record, such as next to the data tabs 89B. Thus, if a user/physician starting examining a patient by reviewing the patient's medical record, the user/physician could jump from the medical record window, such as window 80C, to window 60A to start the diagnosis.

Logout selector 84 of window 80A of FIG. 8A allows the user to logout from the system. Diagnosis questions selectors 85 provides a user with diagnosis specific questions that are specific to the disease previously selected from the list 30. The various diagnosis questions located next to the diagnosis question selectors 85 are utilized by a user to confirm or deny diagnosis of the disease previously selected from list 30. In utilizing selectors 85, a user can toggle between "NO" to "YES" to any number of additional diagnosis questions based upon a patient response.

These additional diagnosis questions that are activated with diagnosis questions selectors 85 enable a user, such as a physician or a nurse to further analyze and diagnose a patient in speaking with and diagnosing a patient. The user can question the patient and ask the patient any number of diagnosis questions to determine what the patient is experiencing, and based on a patient's answers to various questions, a user can appropriately toggle diagnosis questions selectors 85. For instance, in FIG. 8A, window 80A illustrates various diagnosis questions associated with pneumonia whereby a user can toggle "yes" or "no" to any number of diagnosis questions. In one embodiment of the present invention, the diagnosis questions are preferably questions related to the particular disease previously listed from list 30 and may also include other questions to determine if the patient is suffering from some other sickness. For example, in Window 80A, pneumonia is illustrated in window title block 86 as the previously selected disease, so various diagnosis questions are presented to a user whereby that user may present those questions to a patient, such as "Do you have cough," "Do you bring up sputum," "Do you have chest pain on deep breath," and so on. A user can answer "yes" or "no" to any number of questions based upon a patient's response to various questions or based upon a user's own analysis and diagnosis of the patient.

Window 80A may also be configured to include a submit selector 87 as illustrated in FIG. 8B. Submit selector 87 may be located at the bottom of window 80A. After a user answers "yes" or "no" to the various diagnosis question selectors 85, a user can select submit selector 87. When a user chooses submit selector 87, a user may be brought to window 90A of FIG. 9A. FIGS. 9A-9D illustrate window 90A which may be displayed after a user chooses submit selector 87. Window 90A may illustrate treatment options that are linked to the disease that a user has selected out of list 30 of FIG. 6C.

In one embodiment, the present invention is configured so that it acts as a gatekeeper in that the various treatment options illustrated in FIGS. 9A-9D are only presented to a user if a certain threshold or cutoff point score is met. The threshold score is calculated based upon an algorithm that takes into account the answers to the various diagnosis questions illustrated in FIGS. 8A-8B, and if a certain diagnostic criteria or threshold is met, then the various treatment options will be presented to the users.

In one embodiment of the present invention, the algorithm employed by the present invention takes into account a likelihood ratio of certain signs, symptoms, or clinical data. The clinical data may be obtained from various medical resources, literature, or expert opinion. The present invention may be linked to an external database which contains the clinical data and is configured so that the present invention may access and utilize this clinical data. The algorithm also takes into account the relative strength of certain clinical data compared to other clinical data which are cardinal/main features of a certain diagnosis. In one embodiment, this relative strength can be calculated by an expert ranking the importance of each clinical data that is related to a certain diagnosis. Then, the present invention may reorganize the calculated weight based on previous steps and then change the relative weight proportionally to accommodate the cutoff points.

In one embodiment of the present invention, the likelihood ratio for each sign and symptom is calculated from the known ratio of sensitivity/(1−specificity). The highest weight of any clinical data is then converted to one (1) and weights related to other clinical data are assigned accordingly. For example, a weight of 1 will be applied to any sign or symptom that is considered very important. Then, after assigning a weight of 1, the other signs or symptoms will be compared with the very important sign or symptom (one that was assigned weight or power of 1) to isolate the symptoms that are weaker than the very important sign or symptom for the particular disease selected by a user from list 30. A value of less than 1 is then assigned to the weaker symptoms. The strongest symptoms for the particular disease selected by a user are ranked and the strongest symptoms are assigned a weight based on the importance of the signs or symptoms. The present invention will assign a specific weight to each symptom presented to a user via the various diagnosis questions selectors 85. When the total weight (after addition of the weight of all of the signs and symptoms present in a particular patient) reaches a set cut-off or threshold point, then the present invention will evaluate if the selected criteria, or selected signs or symptoms, is reasonable for a certain diagnosis.

The set cut-off or threshold point to determine a diagnosis and provide a user with the treatment data may be a value of 4 or 5, or may be a range, such as 3-6, based on clinical data or known facts that a user may choose. The total weight is determined by adding up the values of the individual weights assigned to each of the symptoms that were identified with a "yes" at diagnosis questions selectors 85 indicating that a patient is experiencing a certain symptom. This set cut-off point is not a limitation of the present invention but merely an example and other embodiments may utilize other cut-off points.

If the total weight of all the signs and symptoms that a patient is experiencing and that was identified by a user reaches the set threshold value, the present invention will evaluate the symptoms that were selected as occurring, via diagnosis questions selectors 85, and evaluate if the selected symptoms are reasonable for a certain diagnosis of the disease previously selected by a user from the list 30. If the selected group of symptoms does not justify the diagnosis for the selected disease, then the present invention may reduce the weight assigned to the less important symptoms to prevent a false positive diagnostic confirmation. The presence or absence of some symptoms for a particular disease may be considered a preventive factor and assigned a negative weight to assist in preventing an incorrect diagnosis. The negative value will reduce the overall weight which could reduce an overall weight below the threshold value. This determination can be based upon clinical data. For example, if a patient's age is less than 40, there is less likely a chance for the patient to get myocardial ischemia. When a patient is 38 years old, then they may get a minus one (−1) for age factor for coronary artery disease. Still that patient can meet cut-off criteria after adding scores for other present symptoms; but the other symptoms' score must be stronger in order to overcome the reduced weight for minus one (−1) from the patient's age.

In one embodiment of the present invention, while the user inputs the various signs and symptoms in list 61, additional data that may be considered important to the diagnosis may be obtained from the patient's electronic medical record such as that illustrated in window 80C. For example, the present invention may obtain data from a patient's medical record, such as a user's age, weight, medical history, allergies, medication list, and social history. Such data may be obtained from the medical record and analyzed along with other data input by a user/physician in determining the total weight and whether the threshold value is met in determining if various treatment options, such as laboratory and radiological studies, for a particular diagnosis will be displayed to a user—with respect to window 90A as illustrated in FIGS. 9A-9D.

In alternative embodiments of the present invention, the absence of certain symptoms from a diagnosis may be considered a weight of zero instead of a negative value. And in other embodiments, nonspecific signs and symptoms selected by a user via diagnosis questions selectors 85 may be assigned a smaller weight such as 0.1 to 0.5. For example, vomiting is not strongly associated with pneumonia. But sometimes it is present as a symptom. Usually fever or productive cough is almost invariably present in case of pneumonia. In such a scenario for pneumonia, both fever and productive cough will be assigned a weigh of one (1) but vomiting will be assigned weight of 0.2 as it is less important than fever or productive cough. After all of the weights have been assigned and all analysis performed for determining if the selected symptoms are reasonable for a certain diagnosis, then if the selected symptoms are reasonable for the selected disease, then the treatment data, such as that illustrated in FIGS. 9A-9D will be presented to a user.

Window 90A illustrates back selector 81, search selector 82, EMR selector 83, logout selector 84, and back to result selector 91. Back to result selector 91 allows a user to return to the list of ranked and sorted high probability differential diagnosis and the list of ranked and sorted low probability differential diagnosis, such as that illustrated in window 60B of FIG. 6C.

Window 90A also illustrates information block 92. Information block 92 is an area of window 90A that displays information about the patient that was gathered during the diagnosis process, such as the chief complaints, the history of present illness, and the review of system. The chief complaints lists the patient's complaints, the history of present illness lists and symptoms that the patient has identified as experiencing, and the review of system may identify symptoms that the patient does not have. These items in information block 92 are examples of the information and format of information that may be illustrated and is for example purposes only and is not to be construed as a limitation of the present invention. The present invention may be configured to illustrate additional or less information in different embodiments.

In one embodiment, the present invention may also be configured so that window 90A also includes assessment plan 93. Assessment plan 93 is an area of window 90A that provides a user with an assessment plan associated with the previously selected disease illustrated in window title block 86 and based upon the diagnosis associated with the information gathered in the present invention, such as window 80A and the user's diagnosis of the patient. In one embodiment of the present invention, assessment plan 93 may present a user with various options for a user to analyze and possibly select/choose for the patient. For example, in window 90A of FIG. 9A, the present invention may provide a user with the choice of "Patient needs to be seen by provider," illustrated by item 94 and/or "Calculate Curb" illustrated by item 95. In additional to items 94 and 95, the present invention may present several other items, such as those illustrated in FIGS. 9B-9D. FIGS. 9A-9D illustrate sample screen shots of an example operation performed by one embodiment of the present invention. The present invention is not limited by its application to the screenshots illustrated by FIGS. 9A-9D.

FIG. 9B illustrates many additional choices presented to a user, such as laboratory and radiological studies 96 and treatment 97. Laboratory and radiological studies 96 presents a user with many different studies/tests that a user can select to be performed for the patient. In one embodiment, the present invention may provide a user with a list of options illustrated by list 96A. A user may then select any number of laboratory and radiological studies from list 96A, such as chest X-ray, blood culture, or complete blood count.

In one embodiment of the present invention, when a user, such as a physician, selects a study/item from list 96A, the user is able to send an order for the selected study to the appropriate individuals and/or lab to order the selected item from list 96A while the user is still documenting his/her encounter with a patient. Thus, there is no need for the user to go to a different computer screen or to have to manually write an order to be processed by another person. This ability helps reduce time associated with ordering tests/studies and improves work flow for the user.

Figure 9A:
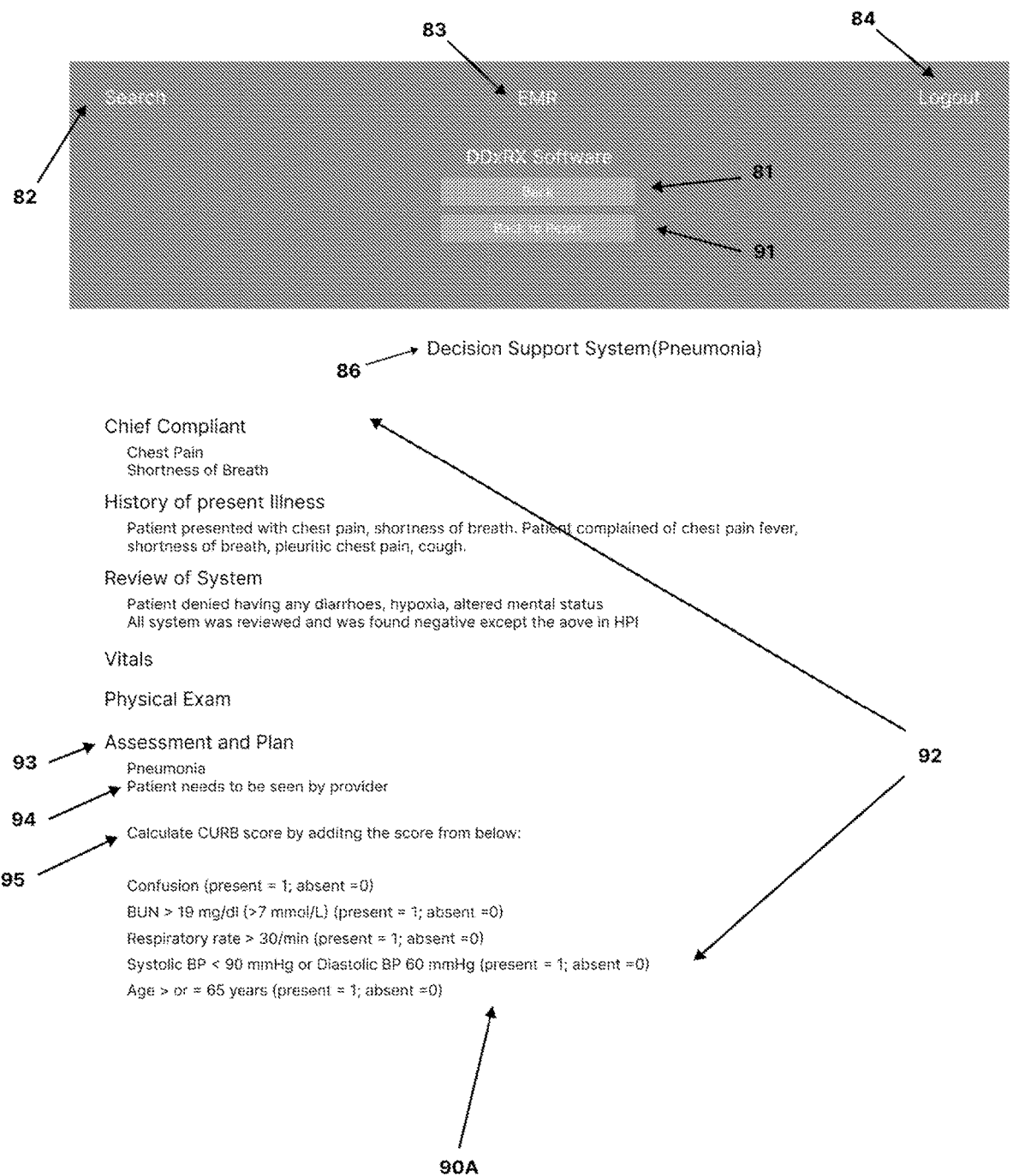
Figure 9C:
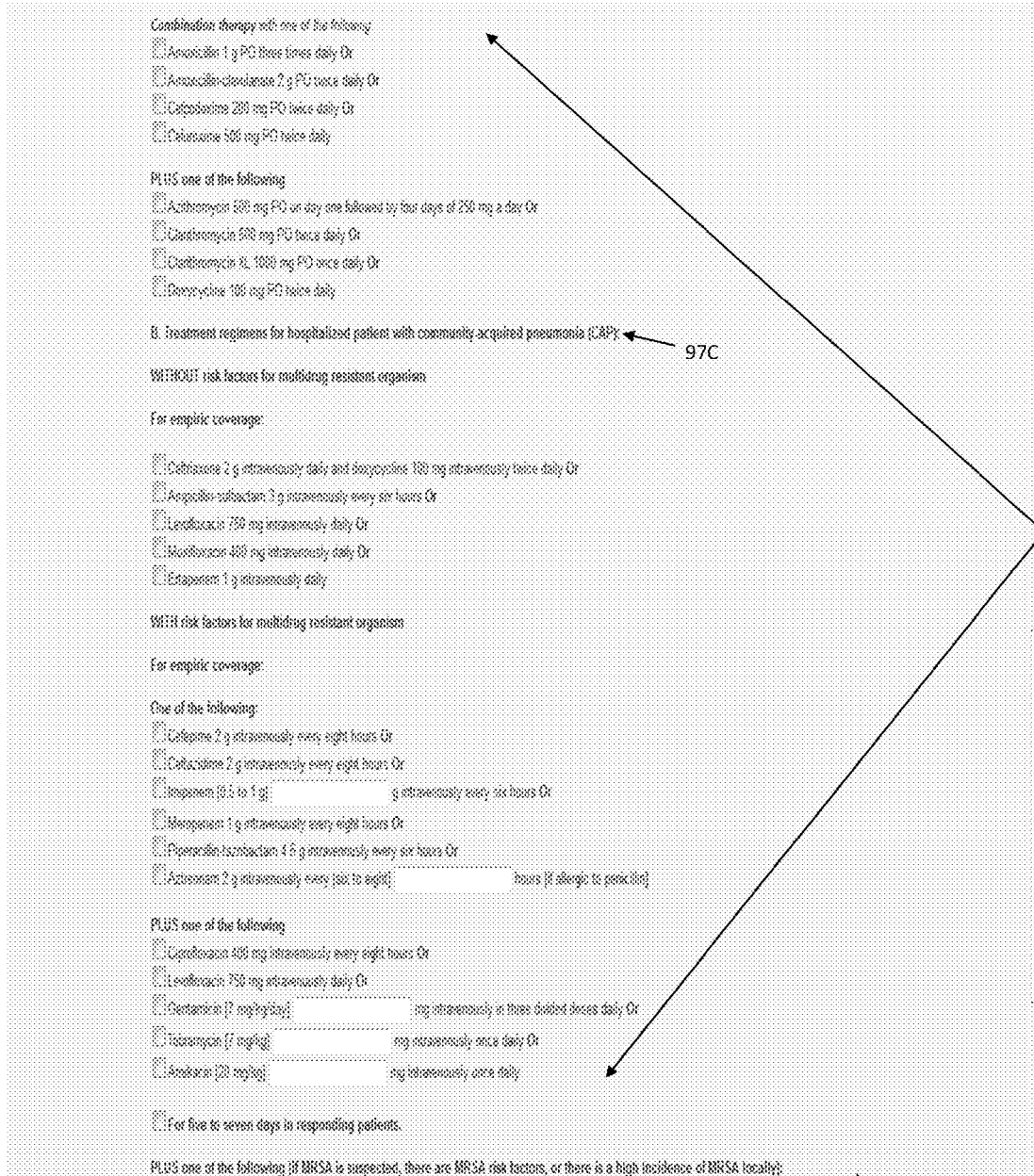
Figure 9D:
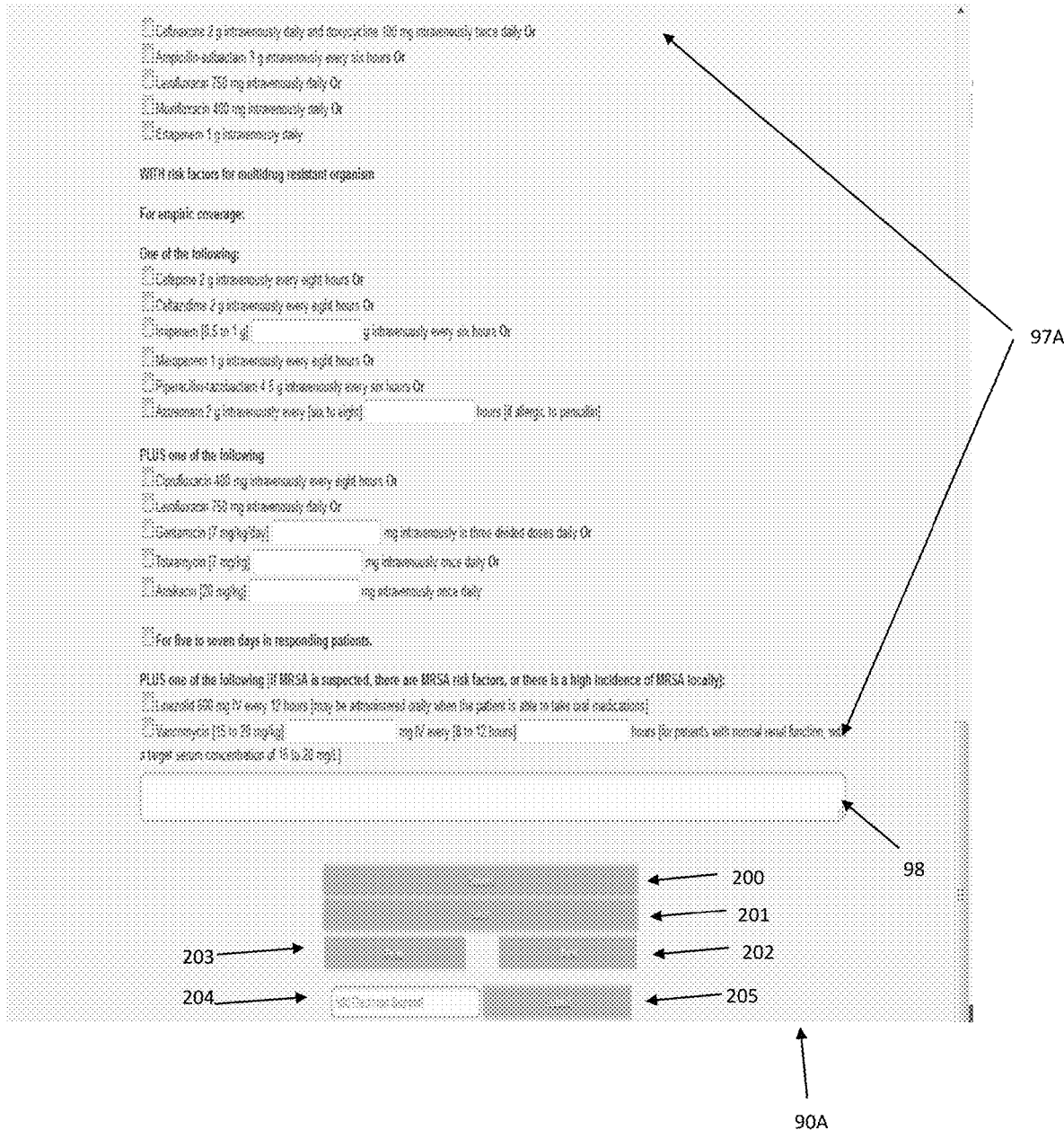

Treatment 97 of window 90A of FIG. 9B presents a user with many treatment options for a user, such as a number of different drugs that can be prescribed for the patient. In one embodiment, the present invention may provide a user with a list of options illustrated by list 97A. List 97A may be an extensive list as illustrated in FIGS. 9B-9D with many different options. The list 97A may also consist of sub-categories as illustrated by sub-category 97B in FIGS. 9B and 97C in FIG. 9C. The sub-categories 97B and 97C may be presented to further limit and/or identify possible treatment options based upon different factors associated with the disease, the patient, and/or the diagnosis information previously gathered, such as the information selected in window 80A.

The present invention may also include a free form text box 98 illustrated in window 90A of FIG. 9D. Free form text box 98 provides a user with the ability to enter additional information, notes, instructions, or information that may be needed with the treatment selected from list 97A. In one embodiment, a user may enter in a specific type of treatment and/or medicine to be used with a patient if that treatment is not included in list 97A. List 97A of treatment 97 allows a user to issue medication orders from simply selecting a box from list 97A. In selecting a treatment option from list 97A, the present invention allows a user to send an order for the selected treatment/medication from list 97A while the user is still documenting his/her encounter with a patient. Thus, there is no need for the user to go to a different computer screen or to have to manually write a medication order. This ability helps reduce time associated with ordering treatment and improves work flow for the user.

The lists illustrated in FIGS. 9B-9D is merely an example embodiment that is limited to pneumonia and other factors chosen for the purpose of illustration only and is not a limitation of present invention. Different diseases may have different lists 97A. FIG. 9D also illustrates the end of list 97A and various options that may be presented to a user after the treatment has been selected, such as submit selector 200, save selector 201, next selector 202, print selector 203, a second submit selector 205 and decision support box 204, which all may be located at the bottom of window 90A.

Figure 9E:
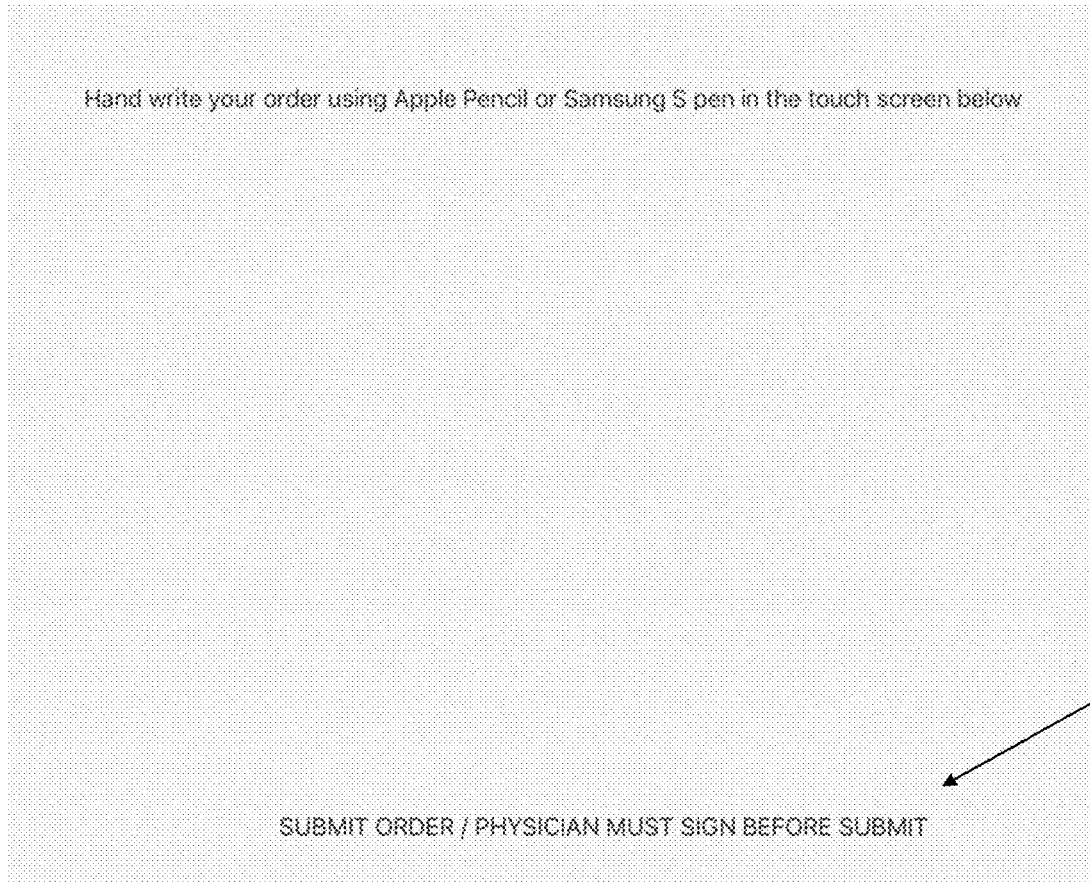

In one embodiment, after a user is brought to window 90A, the present invention may be configured with a button or selector whereby a user can activate such a button or selector and the present embodiment will provide a user with an order entry screen. The present invention may be configured so that after a user selects an option to go to the order entry screen, the user is presented with order entry window 90B illustrated by FIG. 9E. Window 90B illustrates a blank page with margin (can have a margin to mimic paper chart) where a user/physician can type in window 90B using keyboard or handwrite using a pen in an electronic medium like a regular page. Physician can freely enter any type of information for the order, such as laboratory and radiology orders. For example, a physician can enter medication amounts and doses. Physician can handwrite free text messages whereby the user/physician is not required to follow a certain order style (for example, no need to fill out any mandatory box, explain any order or procedure, and no need to fill anything unless he or she would like to—just as if the user/physician were writing in a paper chart In one embodiment, the present invention can be configured so that the user/physician also has the ability to enter hand-written notes and data into a patient's medical record in the same fashion as described with respect to window 90B of FIG. 9E. Thus, if at any time a user/physician would like to enter handwritten text to a patient's medical record, the user could take action to get back to the patient's medical record, such as that illustrated in window 80C of FIG. 8D, and then enter free form handwritten text to the medical record. In such an embodiment, the medical record may be configured with a notes tab within data tabs 89B so that a user could select that tab and then have the ability to freely enter handwritten text.

For example, a physician can use the order page, such as window 90B to order a medication for a given patient. In doing so, a physician can order the medication two ways. If physician (or nurse) uses a touch screen computer, then he or she can use a pen to hand write orders in an electronic medium or he or she can type the order using a keyboard in a free text order form.

Figure 9F:
Figure 9G:

All laboratory and radiology order instructions will accept free form text written orders or hand-written electronic medium orders. The present invention may also be configured with submit order selector 99 so that when a user is finished entering text/notes, the user can depress selector 99 so that the order is processed and delivered to the appropriate persons. When the physician/user is finished entering text in the window 90B, a medical technician can then convert the physician text orders into standard orders like a standard paper chart system. However, the physician is not required to take any further action regarding the free-text order. For example, FIG. 9F illustrates a sample order entry screen, window 90B, after a doctor has freely entered handwritten text into the order entry screen. After the user/physician enters the handwritten text, the user/physician can select the submit order selector 99 and process the order. FIG. 9G illustrates a sample order entry screen, window 90C, after a user/physician has entered text via a keyboard, smartphone, tablet, or other similar application.

In one embodiment, after the user, such as a physician, has input any additional notes into the order entry screen in window 90B, the information input by a physician can be stored in a patient's electronic medical record. In addition, any data input by a user, such as a physician, in the order entry screen can be delivered to a medical technician's inbox and may be accessed by a third party, such as a medical technologist or unit secretary, who will then be able to save physician time by converting/transmitting the physician's order to text orders into standard orders like a standard paper chart system and then may transfer the order to the specific department or person while the physician enters hand written order or free text typed orders in order entry screen. This saves major frustrations of physicians during patient care delivery.

In window 90A, a user may also be able to specifically enter a specific medication if it was not present in window 90A. In entering such information, the present invention is capable to auto correct the medication name based on pharmacy inventory. In addition, standard dose information may also appear when certain medication is selected. In some embodiments, the present invention allows the physician to type dose, route and duration. After the treatment has been chosen by a physician, the present invention may also be configured to send any need for corrections via text messages sent through mobile device notification where physician will be able to accept, deny or modify certain orders from a secure web based order entry form. The physician or nurse's documentation system will accept hand writing while using pen in touch screen in an electronic medium.

Submit selector 200 of FIG. 9D allows a user to submit all orders, such as laboratory and radiological orders, any lab orders, and any medication orders that were selected while documenting the physician encounter note which will be transferred to CPOE (computerized physician order entry). That means the present invention may also be configured so that when submit selector 200 is activated, the orders may be electronically copied to the computerized physician order entry or CPOE. This will reduce physician time to finish encounter as selecting a certain treatment will transfer information into physician progress notes as well as CPOE at the same time. Thus, the physician will be able to order while typing the encounter note without changing tabs or moving to order entry tab. Also when submit selector 200 is selected, the various orders are sent to the appropriate third parties, such as nurses, therapists, other physicians, labs, pharmacies and the like.

Figure 10:
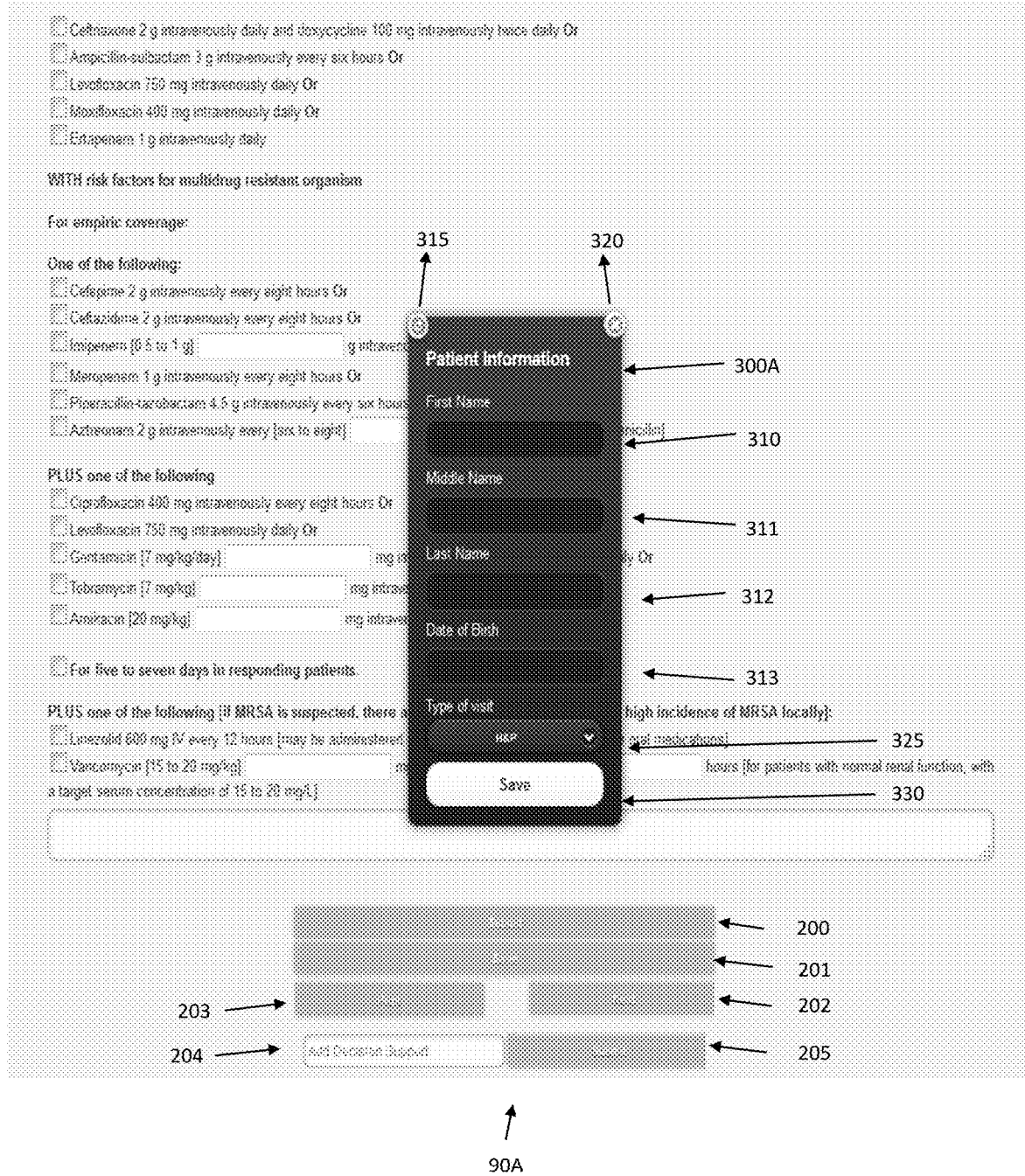
FIG. 10 illustrates a screen shot of an embodiment of the present invention.

Save selector 201 provides a user with the ability to save the current information with the specific patient that is being diagnosed. In one embodiment of the present invention, the user is able to save all of the diagnostic information, radiological and laboratory information, treatment information, and progress notes to the electronic medical record associated with the patient that is in the process of being diagnosed and treated. When a user chooses save selector 201, patient information sub-window 300A, as illustrated in FIG. 10, may be presented to the user. In one embodiment, patient information sub-window 300A pops-up in window 90A as illustrated in FIG. 10.

Once patient information sub-window 300A pops-up in window 90A, a user has the ability to enter patient information into first name field 310, middle name field 311, last name field 312, and date of birth field 313. By inputting the various information, a user is able to properly identify a patient so that any information that is to be saved, will be saved and linked to the correct medical record associated with the patient that is currently being diagnosed and examined. Sub-Window 300A also presents a user with the ability to create an electronic medical record for a patient that does not already have an electronic medical record. Thus, through save selector 201, a user is given the ability to create an electronic medical record for the patient and is also able to save all progress notes, orders, and other data to the electronic medical record for the patient.

Sub-window 300A may also include undue selector 315, close selector 320, type of visit selector 325, and save selector 330. Undue selector 315 allows a user to clear all information/data that was entered into any of fields 310-313 if any mistakes were made or if incorrect information was entered so that a user can enter new information. Close selector 320 allows a user to close sub-window 300A and return to window 90A. Type of visit selector 325 allows a user to select the type of visit associated with the patient that a user is currently diagnosing. In one embodiment, a user may be able to choose several different types of pre-defined entries for the type of visit, such as H&P for history and physical to identify the type of visit with type of visit selector 325. A user may also be able to choose progress note with type of visit selector 325. Save selector 330 allows a user to save the current diagnosis or other information with the specific patient that is being diagnosed and that was identified with sub-window 300A.

In one embodiment, when a user saves information by activating save selector 330, a user may be brought to a database of medical records whereby a user may be able to edit, view and access the details of the patient's medical records.

As illustrated in window 90A of FIG. 9D, a user may also choose print selector 203. By choosing print selector 203, the present invention may print out the current data associated with the patient in a report format configured for easy reading. In addition, a user may choose second submit selector 205. Here a user can type in the empty search box 204 any disease they want. Once a disease is selected from the drop down box, use can select the disease and select second submit selector 205 which will add the treatment protocol for that disease inside the physician encounter note. Now user can select the empty boxes, such as those in list 97 A and incorporate laboratory and radiological treatments inside the progress note as well as add those orders into CPOE for selecting submit selector 200.

As illustrated in window 90A of FIG. 9D, after a user performs diagnosis and chooses which laboratory and radiological tests and which treatment to be provided, then a user may select next selector 202. Next selector 202 allows a user to depress it so that a user can be brought to window 400A of FIG. 11. Window 400A of FIG. 11 provides a user with a summary of data associated with the diagnosis and treatment of the patient which may include any number of data fields located in information block 92, such as the chief complaints field 401, the history of present illness field 402, a review of system field 403, and a physical exam field 404. Window 400A of FIG. 11 may also include the assessment plan 93. These fields are merely examples and are not limitations of the present invention as any number of data fields may be displayed in window 400A.

Chief complaints field 401 may display the main complaints of the patient when a user began to examine the patient. History of present illness field 402 preferably illustrates the positive findings and symptoms that the patient experienced and/or complained of while undergoing examination by the user. Review of system field 403 is an area of window 400A that illustrates the negative findings or list of any number of symptoms and signs that the patient did not complain of and/or that a user did not find when examining the patient. Physical exam field 404 identifies various physical properties/data about the patient that the user identified while conducting a physical exam of the patient. Window 400A also illustrates assessment plan 93, which, in Window 400A of FIG. 11, illustrates the current treatment plan chosen for the patient that has been ordered by a user such as the medicines prescribed and a list of the lab tests and studies ordered by the user.

As further illustrated in FIG. 11, window 400A may also be configured to include a submit selector 410, a save selector 411, a second submit selector 412, and decision support box 413, located at the bottom of window 400A.

Save selector 411, similar to save selector 201 of window 90A of FIG. 9D provides a user with the ability to save the current information with the specific patient that is being diagnosed. Thus, in activating save selector 411, patient information sub-window 300A, as illustrated in FIG. 10, is presented to the user so that the user can proceed in saving data. Second submit selector 412 of window 400A works like 205. And search box 413 works like 204.

Figure 12:
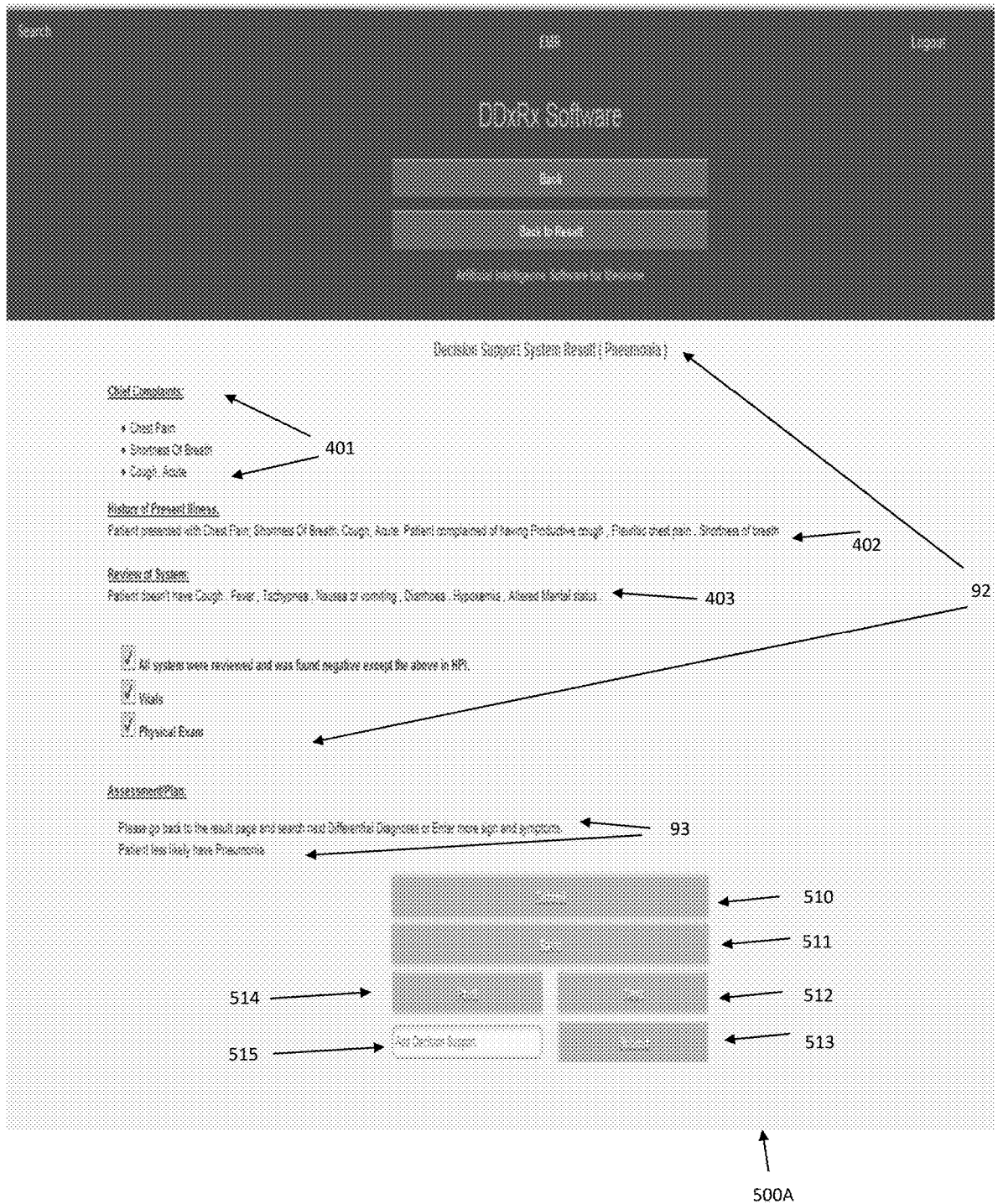
FIG. 12 illustrates a screen shot of an embodiment of the present invention.

In one embodiment of the present invention, when a user is examining a patient, depending upon the condition of the patient, it is possible that the threshold score and/or certain diagnostic criteria calculated by the present invention will be lower than the minimum threshold such that the various treatment options, such as laboratory and radiological studies 96 and treatment 97, set forth in window 90A as illustrated in FIGS. 9A-9D will not be displayed to a user. In this scenario, the present invention may bring a user to a no-treatment window 500A illustrated in FIG. 12. As illustrated in FIG. 12, no-treatment window 500A may provide a user with various data associated with a response generated by one embodiment of the present invention after the present invention has determined that treatment options will not be provided to a user because the threshold has not been satisfied. In determining the threshold, the present invention has analyzed various data such as the disease chosen by a user from one of the diseases listed in high probability differential diagnosis list 30 and the user's responses to diagnosis question selectors 85 of FIGS. 8A-8B.

As illustrated in FIG. 12, no-treatment window 500A may include various data/information, such as an information block 92. Similar to window 90A of FIG. 9A, information block 92 is an area of no-treatment window 500A that displays information about the patient that was gathered during the diagnosis process, such as the chief complaints field 401, the history of present illness field 402, and the review of system 403. These fields are merely examples and are not limitations of the present invention as any number of data fields may be displayed in no-treatment window 500A.

Chief complaints field 401 may display the main complaints of the patient when a user began to examine the patient. History of present illness field 402 preferably illustrates the positive findings and symptoms that the patient experienced and/or complained of while undergoing examination by the user. Review of system field 403 is an area of no-treatment window 500A that illustrates the negative findings or list of any number of symptoms and signs that the patient did not complain of and/or that a user did not find when examining the patient. No-treatment window 500A also illustrates assessment plan 93. However, in no-treatment window 500A, assessment plan 93 notifies the user to go back to the result page, such as the result page illustrated by window 60B of FIG. 6C. In one embodiment, in notifying the user to go back to window 60B, the present invention may specifically state that the patient is less likely to have a certain disease or ailment.

In one embodiment of the present invention, no-treatment window 500A may also present various options to a user, such as submit selector 510, save selector 511, next selector 512, a second submit selector 513, print selector 514 and decision support box 515. These options may be located at the bottom of no-treatment window 500A. In one embodiment of the present invention, submit selector 510 allows a user to submit any information gathered during diagnosis to the computerized physician order entry or CPOE. Save selector 511 provides a user with the ability to save the current information to the electronic medical record associated with the specific patient that is being diagnosed and can also allow a user to create a new medical record if the patient does not already have a medical record on file with the user. In doing so, when a user chooses save selector 511, patient information sub-window 300A, as illustrated in FIG. 10, may be presented to the user.

Figure 13:
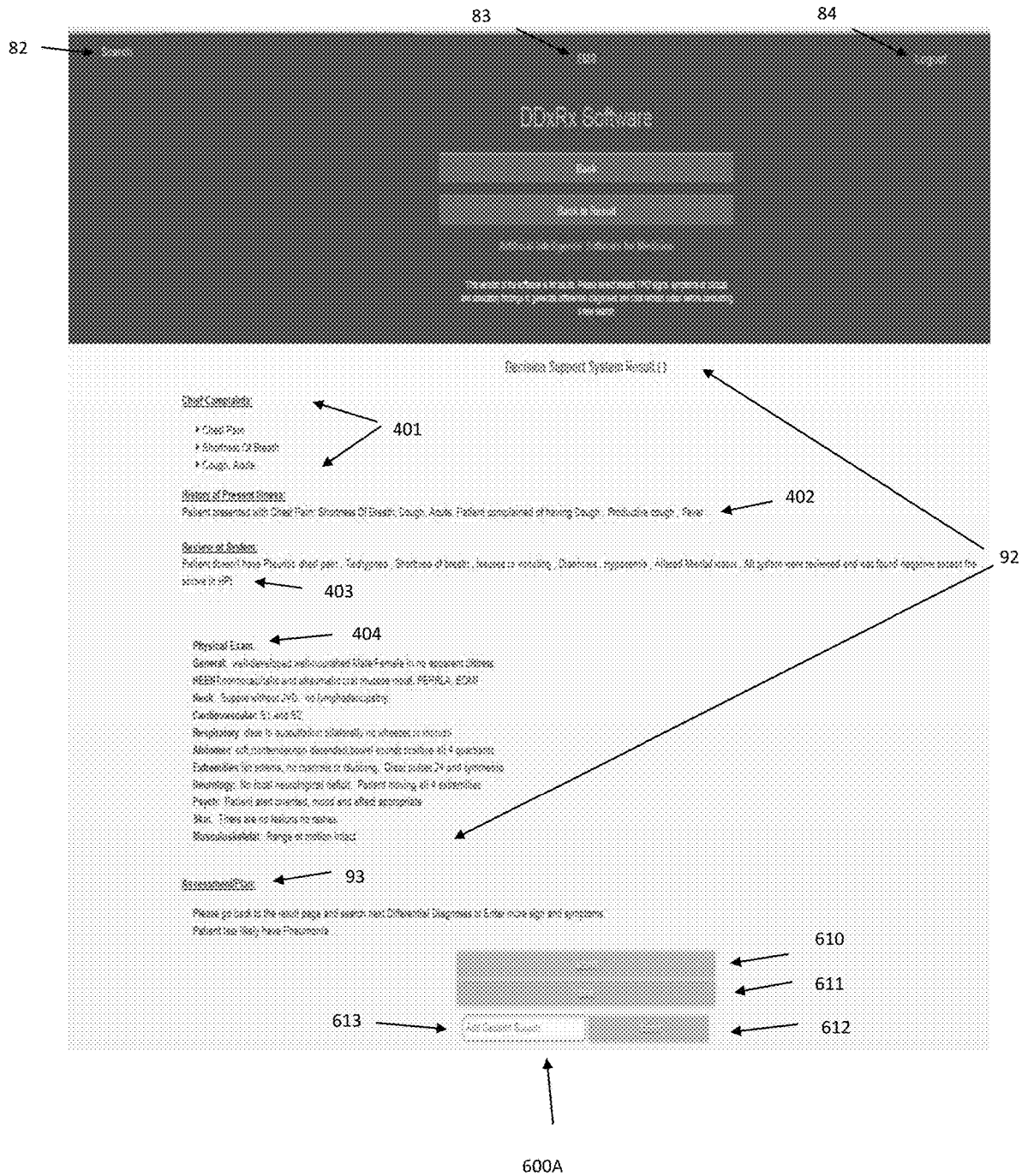
FIG. 13 illustrates a screen shot of an embodiment of the present invention.

In one embodiment, the present invention may be configured so that that when a user chooses next selector 512 of no-treatment window 500A, a user is presented with window 600A of FIG. 13. Window 600A of FIG. 13 is similar to window 400A of FIG. 11. In addition, window 600A also provides a user with a summary of data associated with the diagnosis and treatment of the patient which may include any number of data fields located in information block 92, such as the chief complaints field 401, the history of present illness field 402, a review of system field 403, and a physical exam field 404. Window 600A of FIG. 13 may also include the assessment plan 93. The difference between window 400A and 600A concerns assessment plan 93 of window 600A in that assessment plan 93 of window 600A notifies the user to go back to the result page, such as the result page illustrated by window 60B of FIG. 6C. A user is notified to revisit result page 60B because the present invention has determined that it is likely that the patient is not suffering from the previously selected disease from list 30 of window 60B after the present invention has analyzed the user's answers to diagnosis questions selectors 85.

Thus, as this point in the examination/diagnosis process, a user can select search selector 82 to get back to window 60A of FIG. 6B so that a user can see the previously selected inputs that were selected with input/selection drop down boxes 61 to modify or add additional symptoms to continue the examination process. In an alternative embodiment, search selector 82 can bring the user back to window 60B of FIG. 6C so that user may select a different disease from list 30. Window 600A may also be configured to include a submit selector 610, a save selector 611, a second submit selector 612 (which works like 205), and decision support box 613 (like 204), located at the bottom of window 600A. Save selector 611 allows a user to save the physician encounter note to medical record.

Save selector 611, similar to save selector 201 of window 90A of FIG. 9D provides a user with the ability to save the current information with the specific patient that is being diagnosed. Thus, in activating save selector 611, patient information sub-window 300A, as illustrated in FIG. 10, is presented to the user so that the user can proceed in saving data. These fields and selectors illustrated in FIG. 13 are merely examples and are not limitations of the present invention as any number of data fields and selectors may be displayed in window 600A.

As illustrated in no-treatment window 500A of FIG. 12, a user may also choose print selector 514. By choosing print selector 514, the present invention may print out the current data associated with the patient concerning the examination of the patient. In addition to print selector 514, a user may also choose a second submit selector 513 and decision support box 515, located at the bottom of no-treatment window 500A.

Figure 14:
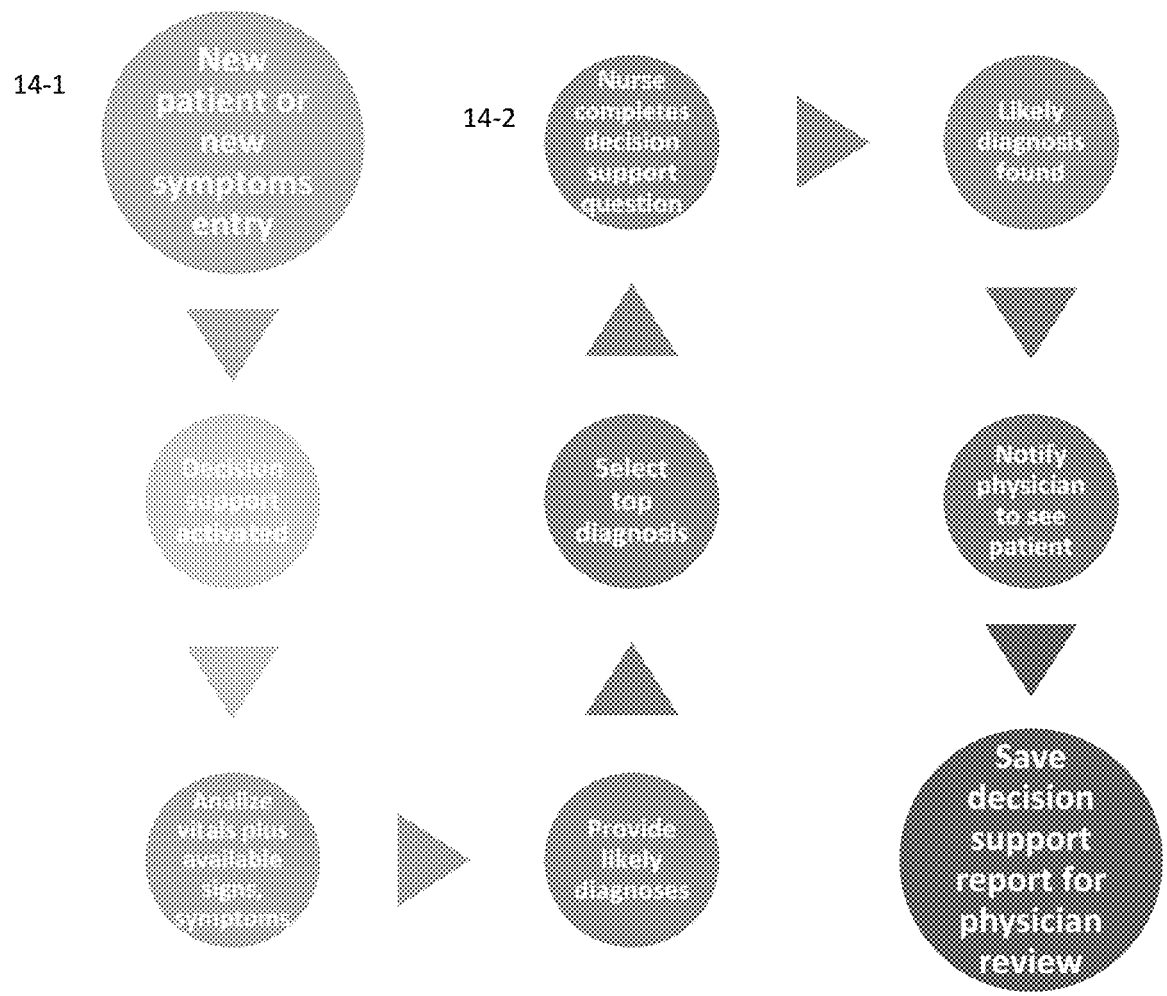
FIG. 14 illustrates a work flow of one embodiment of the present invention.

FIG. 14 illustrates a sample work flow of one embodiment of the present invention illustrating how the embodiment operates with a combined electronic medical record and the combined components to perform a differential diagnosis and generate diagnoses for a user/health care provider. The work flow illustrated in FIG. 14 illustrates how a user, such as a nurse, can use an embodiment of the present invention to help a physician expedite patient care. Once new patient arrives at the triage, a nurse will start by entering the patient's signs and symptoms, as illustrated by 14-1, in the differential diagnosis generator search screen, such as window 60A of FIG. 6B. In addition, the nurse will also collect patient vital signs and enter relevant data in the differential diagnosis generator screen. Once decision supportive activated, there will be multiple high probability differential diagnosis available for the nurse to work with. Nurse will select the top differential diagnoses and ask the patient all questions available and submit answers in the form of Yes or No, as illustrated by 14-2. Once software confirms certain diagnoses, the present invention will also provide treatment protocol which includes laboratory and radiological, microbiology, and medications with exact doses necessary for certain diagnoses. At this point, the nurse will save the available software screen in the electronic medical record and notify the physician to see the patient and complete physician encounter notes. Physician will decide what tests to order by selecting the appropriate tests and choosing medications in the same fashion, such as that illustrated by window 90A. Once selected, a physician may use next selector 202 to pull the refined encounter note and subsequently submit the data in the electronic medical record.

Figure 15:
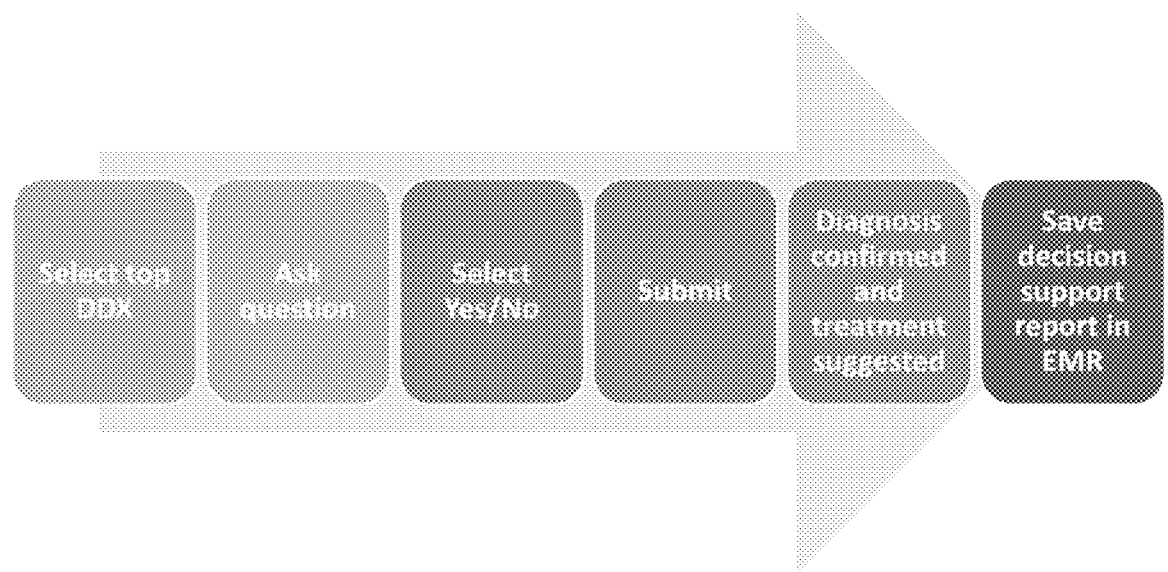
FIG. 15 illustrates a sample work flow of one embodiment of the present invention under a certain scenario.

FIG. 15 illustrates how an embodiment of the present invention may work when multiple differential diagnoses is available for a user to work with. When top differential diagnosis is selected, it provides multiple questions for the patients. The questions are asked to the patient and the questions are answered yes or no based on patient reply, such as that illustrated in window 80A of FIG. 8B. Once all the questions are asked, a user/nurse can submit the answers. If scores (calculated from the answers submitted) are higher than the cutoff point established for a particular disease, then the diagnosis is confirmed. At this point, when the diagnosis has been confirmed, a treatment is suggested and the decision support algorithm is submitted in the electronic medical record.

Figure 16:
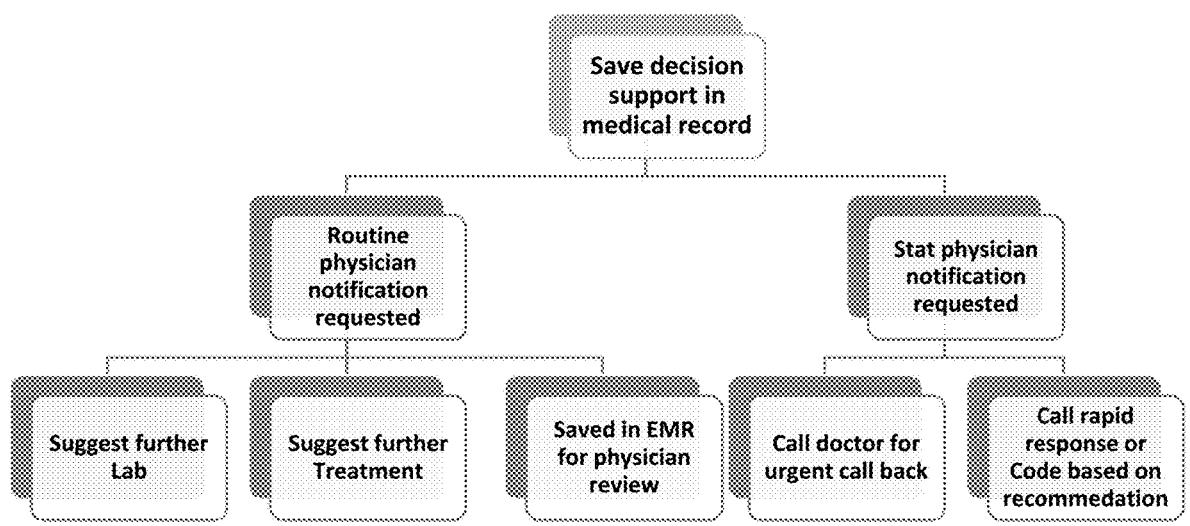
FIG. 16 illustrates a sample work flow of one embodiment of the present invention under a certain scenario.

FIG. 16 illustrates how an embodiment of the present invention can help a nurse to alert physician about initial/starting patient findings. Embodiments of the present invention can assist users with making crucial decisions or notifying others of urgent and emergency situations that simply cannot wait. Based on the available data when entered through the decision support system, the system can alert the nurses whether or not a physician should be contacted as a routine notification or an urgent notification. For example, when dealing with a patient having chest pain and shortness of breath, the two symptoms are entered in the differential diagnosis generator search page, such as window 60A of FIG. 6A, and the present invention can quickly suggest a likely diagnosis. If a diagnosis of pneumonia is confirmed, there will be a set of steps for the nurse to follow. One set of steps may lead to an urgent notification of the physician versus a routine notification. However if myocardial ischemia or any other life-threatening diagnosis is confirmed, instead of pneumonia, an embodiment of the present invention may be configured to alert the nurses to immediately call the physician. Thus, the present invention can assist in identifying a routine notification versus urgent notification through the analysis of symptoms and confirmation of diagnosis.

Figure 17:
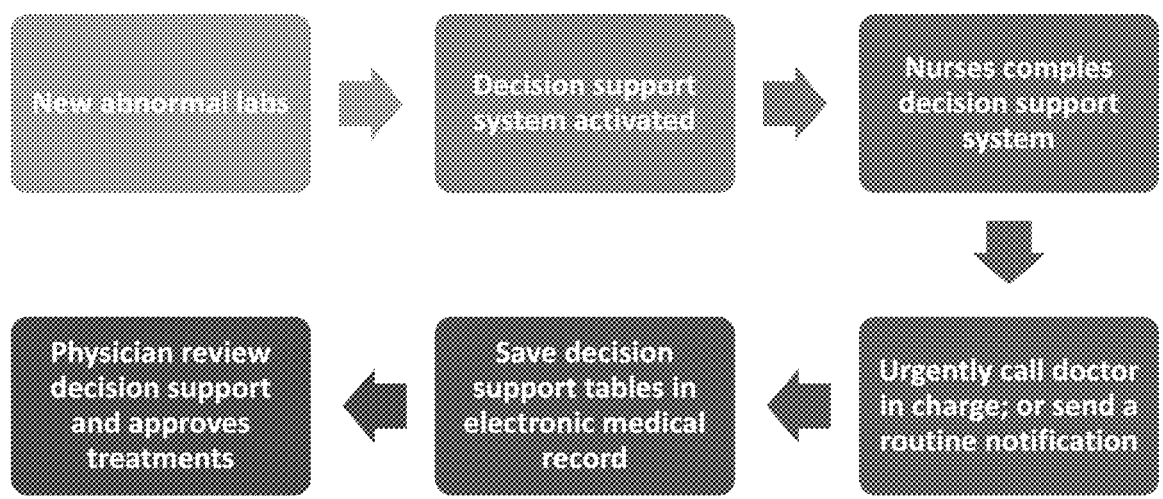
FIG. 17 illustrates a sample work flow of one embodiment of the present invention under a certain scenario.

FIG. 17 illustrates how an embodiment of the present invention can work in the event of an abnormal lab provided to the nurse. In such a situation, a nurse will indicate that there has been an abnormal lab in the differential diagnosis generator. In addition, the nurse will also enter additional data in the differential diagnosis generator search screen—such as hypokalemia, and abnormal heart rhythm as an example. The differential diagnosis generator in such case will suggest some diagnoses. Once all the decision support questions are answered and submitted, the present invention can advise the nurse to either call physician immediately or look for additional data in the patient's chart. Once additional data is included, and decision support is submitted, an embodiment of the present invention can also alert the nurse whether she should call the physician as a routine call or on an emergency basis.

Although the present invention and its advantages have been described in detail, it should be understood that various changes, substitutions and alterations can be made herein without departing from the invention. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized.

What is claimed is:

1. A method for generating a high probability differential medical diagnosis comprising:
    collecting a first medical clinical data from a patient;
    collecting a second medical clinical data from the patient;
    linking said collected first and second medical clinical data with a differential diagnosis medical database, whereby said differential diagnosis medical database includes disease data and medical clinical data related to said disease data;
    comparing said collected first medical clinical data to said disease data in said differential diagnosis medical database, wherein said comparing said collected first medical clinical data comprises:
        comparing said first medical clinical data to said differential diagnosis medical database;
        isolating all disease data common to said first medical clinical data;
        arranging said isolated disease data common to said first medical clinical data into a first grouping; and
    comparing said collected second medical clinical data to said disease data in said differential diagnosis medical database, wherein said comparing said collected second medical clinical data comprises:
        comparing said second collected medical clinical data to said differential diagnosis medical database;
        isolating all disease data common to said second medical clinical data;
        arranging said isolated disease data common to said second medical clinical data into a second grouping;
        isolating all disease data in said differential diagnosis medical database common to said first medical clinical data and said second medical clinical data;
        generating a listing of said isolated common disease data;
        comparing said first grouping of isolated disease data to said second grouping of isolated disease data;
        isolating disease data common to said first grouping and said second grouping;
        ranking said isolated disease data common to said first grouping and said second grouping into a third ranked list; and
        ranking said isolated common disease data in the third ranked list, wherein the position in the third ranked list is based upon:
            the number of times said disease data is associated with said first medical data and said second medical data followed by the relative ranked position of said isolated disease data associated with said first medical data.

2. The method of claim 1, wherein said ranking of third ranked list comprises:
    more prevalent disease data is ranked ahead of less prevalent disease data.

3. The method of claim 1, further comprising: generating a listing of said third ranked list;
    illustrating said generated listing of said third ranked list, wherein said illustrating said generated listing of said third ranked list comprises:
    creating a graphical table of said third ranked list grouping; and illustrating said graphical table.

4. The method of claim 3, further comprising:
    saving said generated listing of said third ranked list; and
    communicating said generated listing of said third ranked list, wherein said communicating of said generated listing of said third ranked list comprises:
        sending said generated listing of said third ranked list in an electronic message.

5. The method of claim 1, further comprising:
    linking each disease data in said third ranked list with diagnosis questions specific to said each disease data in said third ranked list;
    providing a selection means, whereby one of said disease data in said third ranked list may be selected;
    illustrating one or more of said diagnosis questions to a user in response to said selected disease data from said third ranked list, wherein said illustrated diagnosis questions are specific to said selected disease data;
    providing a selection means for said user to answer said diagnosis questions; analyzing said answers to said diagnosis questions; and
    generating data in response to said analyzed answers to said diagnosis questions.

6. The method of claim 5, wherein said generating data in response to said analyzed answers to said diagnosis questions comprises:
    providing diagnostic confirmation and treatment data related to said selected ranked disease data from said third ranked list, wherein said diagnostic confirmation and treatment data provides information related to the treatment of said selected ranked disease data from said third ranked list.

7. The method of claim 6, wherein said analyzing said answers to said diagnosis questions comprises:
    establishing a threshold value to be assigned to said selected ranked disease data from said third ranked list;
    establishing a weight for each answer of said diagnosis questions, whereby a positive response to one of said diagnosis questions will be assigned a first weight and a negative response to one of said diagnosis questions will be assigned a second weight;
    adding up all of said weights assigned to said answers of said diagnosis questions to obtain a total sum;
    comparing said threshold value assigned to said selected ranked disease data from said third ranked list to said total sum of all of said weights;
    generating a diagnosis confirmation signal, wherein said diagnosis confirmation signal is positive only if said total sum equals or exceeds said threshold value assigned to said selected ranked disease data from said third ranked list; and
    said diagnosis confirmation signal is negative only if said total sum is lower than said threshold value assigned to said selected ranked disease data from said third ranked list.

8. The method of claim 7, wherein said generating data in response to said analyzed answers to said diagnostic questions comprises:
    analyzing said diagnosis confirmation signal and illustrating data to said user, wherein if said diagnosis confirmation signal is positive, said illustrated data will include treatment data related to said selected ranked disease data from said third ranked list; and if said diagnosis confirmation signal is negative, said illustrated data will include data notifying a user that said selected ranked disease data from said third ranked list is not a diagnosis.

9. A method of generating a high probability differential medical diagnosis comprising:
- collecting a first medical data from a patient;
- collecting a second medical data from the patient;
- accessing master differential diagnosis medical data tables comprising a plurality of medical data and differential diagnosis data associated with said medical data;
- connecting the first medical data with the master differential diagnosis medical data tables;
- connecting the second medical data with the master differential diagnosis medical data tables;
- isolating all disease data common to said master differential diagnosis medical data tables associated with said first medical data and said second medical data;
- generating a listing of said isolated common disease data associated with said first medical data and said second medical data; and
- arranging said isolated common disease data in said generated listing in a ranked order, whereby the position in said ranked listing is based upon the number of times said disease data is associated with said first medical data and said second medical data followed by the relative ranked position of said isolated disease data associated with said first medical data.

10. The method of claim 9, further comprising:
- ranking said disease data within said master differential diagnosis medical data table associated with said first medical data, whereby more prevalent disease data is ranked ahead of less prevalent disease data.

11. The method of claim 10, further comprising:
- arranging said isolated common disease data in said generated listing in a ranked order, whereby the position in said ranked listing is based upon the medical data that concerns said patient more instead of the first medical data.

12. A method of generating a high probability differential medical diagnosis comprising:
- collecting a first medical data from a patient;
- collecting a second medical data from the patient;
- collecting a third medical data from the patient;
- accessing master differential diagnosis medical data tables comprising a plurality of medical data and differential diagnosis data associated with said medical data;
- connecting the first medical data with the said master differential diagnosis medical data tables;
- connecting the second medical data with the said master differential diagnosis medical data tables;
- generating a listing of said isolated common disease data; and
- arranging all of said isolated common disease data in said generated listing in a ranked order, whereby the position in said ranked listing is based upon the number of times said disease data is associated with said first medical data table, said second medical data table, and said third medical data table followed by the relative ranked position of said isolated disease data within said first medical data table followed by the relative ranked position of said isolated disease data within said second medical data table.

13. The method of claim 12, further comprising:
- ranking said disease data within said differential diagnosis medical data table associated with said first medical data, whereby more prevalent disease data is ranked ahead of less prevalent disease data; and
- ranking said disease data within said differential diagnosis medical data table associated with said second medical data, whereby more prevalent disease data is ranked ahead of less prevalent disease data.

* * * * *